United States Patent
Blancou et al.

(10) Patent No.: US 11,577,082 B2
(45) Date of Patent: Feb. 14, 2023

(54) TREATMENT OF INFLAMMATORY DISORDERS

(71) Applicants: Galvani Bioelectronics Limited, Middlesex (GB); Université Côte d'Azur, Nice (FR); Centre Nationale de La Recherche Scientifique, Paris (FR)

(72) Inventors: Philippe Blancou, Nice (FR); Nicolas Glaichenhaus, Nice (FR); Arun Sridhar, Stevenage (GB)

(73) Assignees: Galvani Bioelectronics Limited, Middlesex (GB); GlaxoSmithKline Intellectual Property Development Limited, Brentford (GB); Université de Nice Sophia-Antipolis, Nice (FR); Centre Nationale de La Recherche Scientifique, Paris (FR)

( * ) Notice: Subject to any disclaimer, the term of this patent is extended or adjusted under 35 U.S.C. 154(b) by 95 days.

(21) Appl. No.: 16/347,940

(22) PCT Filed: Nov. 8, 2017

(86) PCT No.: PCT/EP2017/078677
§ 371 (c)(1),
(2) Date: May 7, 2019

(87) PCT Pub. No.: WO2018/087193
PCT Pub. Date: May 17, 2018

(65) Prior Publication Data
US 2019/0290913 A1    Sep. 26, 2019

(30) Foreign Application Priority Data
Nov. 8, 2016 (GB) .................................... 1618838

(51) Int. Cl.
*A61N 1/36* (2006.01)
*A61N 1/372* (2006.01)

(52) U.S. Cl.
CPC ..... *A61N 1/36139* (2013.01); *A61N 1/36007* (2013.01); *A61N 1/36157* (2013.01); *A61N 1/36171* (2013.01); *A61N 1/37211* (2013.01)

(58) Field of Classification Search
CPC .............. A61N 1/0551; A61N 1/36007; A61N 1/3605; A61N 1/3606; A61N 1/36057;
(Continued)

(56) References Cited

U.S. PATENT DOCUMENTS 9,415,220 B1    8/2016  Spinelli
2005/0075701 A1*  4/2005  Shafer ................ A61N 1/36017
                                                               607/72
(Continued)

FOREIGN PATENT DOCUMENTS

WO    WO 2013/086175 A1    6/2013

OTHER PUBLICATIONS

Guyot, M., Simon, T., Panzolini, C., Ceppo, F., Daoudlarian, D., Murris, E., . . . & Blancou, P. (2019). Apical splenic nerve electrical stimulation discloses an anti-inflammatory pathway relying on adrenergic and nicotinic receptors in myeloid cells. Brain, behavior, and immunity, 80, 238-246. (Year: 2019).*
(Continued)

*Primary Examiner* — Carl H Layno
*Assistant Examiner* — Jane C Kalinock
(74) *Attorney, Agent, or Firm* — Banner & Witcoff, Ltd.

(57) ABSTRACT

Devices and methods for the stimulation of neural signaling of an apical splenic nerve, the device having a transducer for placement on or around the apical splenic nerve, and a signal generator to generate a signal that stimulates or inhibits the neural activity of the apical splenic nerve to produce a
(Continued)

physiological response. The transducer has at least one electrode, and the signal generator is a voltage or current source. The stimulation electrical signal has a frequency of between 1 Hz and 50 Hz.

30 Claims, 14 Drawing Sheets

(58) Field of Classification Search
CPC ............ A61N 1/36139; A61N 1/36157; A61N 1/36171; A61N 1/37211
USPC .......................................................... 607/116
See application file for complete search history.

(56) References Cited

U.S. PATENT DOCUMENTS

| | | |
|---|---|---|
| 2005/0075702 A1 | 4/2005 | Shafer |
| 2006/0287678 A1 | 12/2006 | Shafer |
| 2011/0160798 A1 | 6/2011 | Ackermann et al. |
| 2015/0174397 A1 | 6/2015 | Bhadra et al. |
| 2017/0120046 A1* | 5/2017 | Schwab ............... A61M 5/1723 |

OTHER PUBLICATIONS

International Search Report and Written Opinion dated Dec. 20, 2017 issued in PCT/EP2017/078677.
R. Medzhitov, Origin and physiological roles of inflammation., Nature 454, 428-435 (Jul. 24, 2008).
J. M. Huston et al., Splenectomy inactivates the cholinergic antiinflammatory pathway during lethal endotoxemia and polymicrobial sepsis., J Exp Med (2006) 203 (7): 1623-1628.
Nance et al., Autonomic innervation and regulation of the immune system (1987-2007)., Brain, Behavior, and Immunity vol. 21, Issue 6, Aug. 2007, pp. 736-745.
Dale et al., The presence of histamine and acetylcholine in the spleen of the ox and the horse., J Physiol vol. 68, Issue 2, Oct. 23, 1929, pp. 97-123.
Cailotto et al., Neuroanatomical evidence demonstrating the existence of the vagal anti-inflammatory reflex in the intestine., Neurogastroenteroly & Motility, vol. 24, Issue 2, Feb. 2012, pp. 191-e93.
Rosas-Ballina et al., The Neurology of the Immune System: Neural Reflexes Regulate Immunity., vol. 64, Issue 1, Oct. 15, 2009, pp. 28-32.
Vida et al., α7-Cholinergic Receptor Mediates Vagal Induction of Splenic Norepinephrine., J Immunol Apr. 1, 2011, 186 (7) 4340-4346.
Bratton et al., Neural regulation of inflammation: No. neural connection from the vagus to splenic sympathetic neurons., Exp Physiol 97, 1180, Nov. 2012.
Martelli et al., Reflex control of inflammation by sympathetic nerves, not the vagus., J Physiol 592(7), 1677. Apr. 1, 2014.
Martelli, et al., , Reflex control of inflammation by the splanchnic antiinflammatory pathway is sustained and independent of anesthesia., Am J Physiol Regul IntegrComp Physiol 307, R1085. Nov. 2014.
Martelli et al., The cholinergic anti-inflammatory pathway: A critical review., Autonomic Neuroscience, vol. 182, May 2014, pp. 65-69.
Koopman FA et al., Vagus nerve stimulation inhibits cytokine production and attenuates disease severity in rheumatoid arthritis., Proc Natl Acad Sci USA, Jul. 19, 2016 113 (29) 8284-8289; first published Jul. 5, 2016.
Buijs R M, et al., Spleen Vagal Denervation Inhibits the Production of Antibodies to Circulating Antigens., PLoS One. Sep. 5, 2008; 3(9):e3152.

* cited by examiner

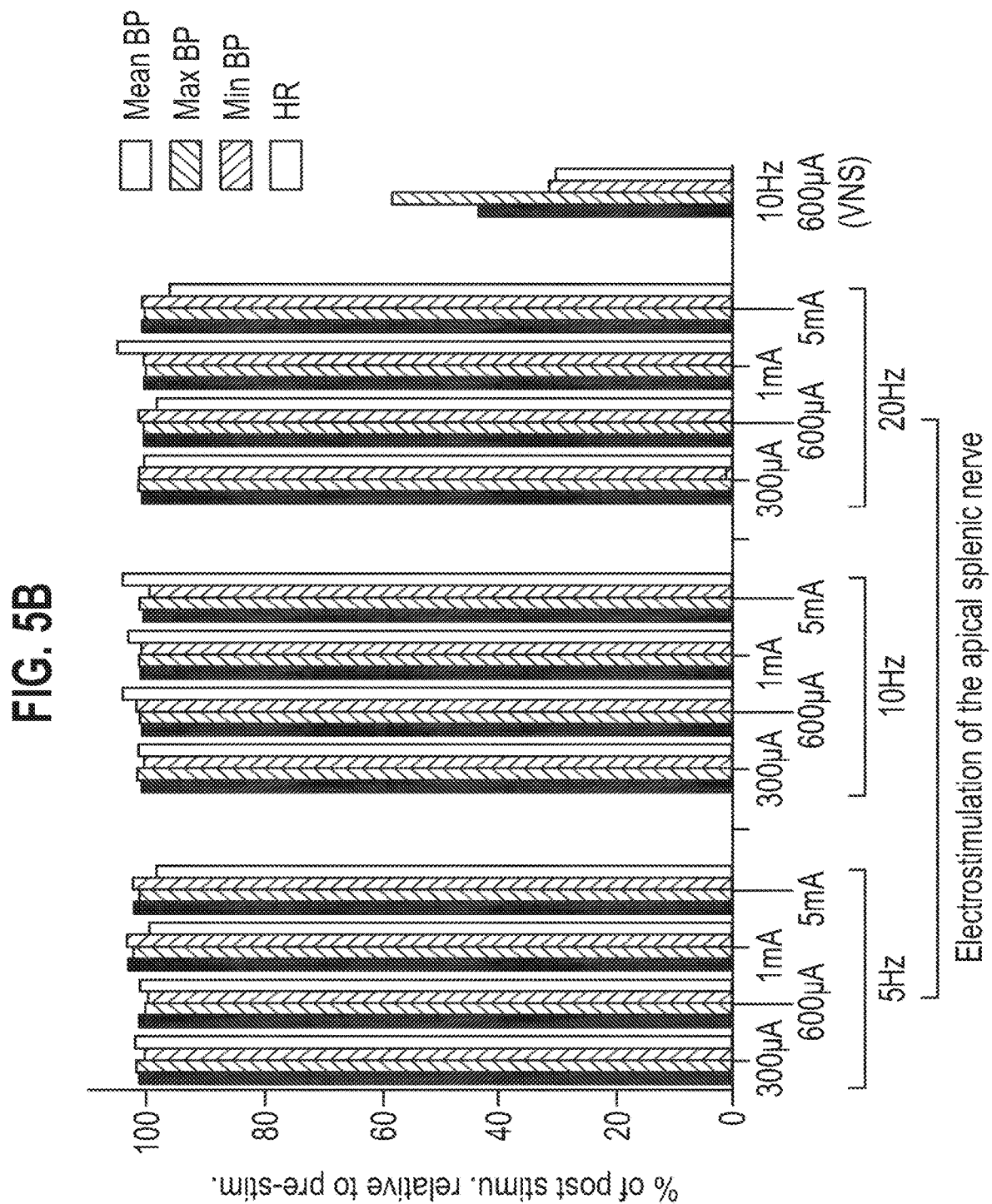

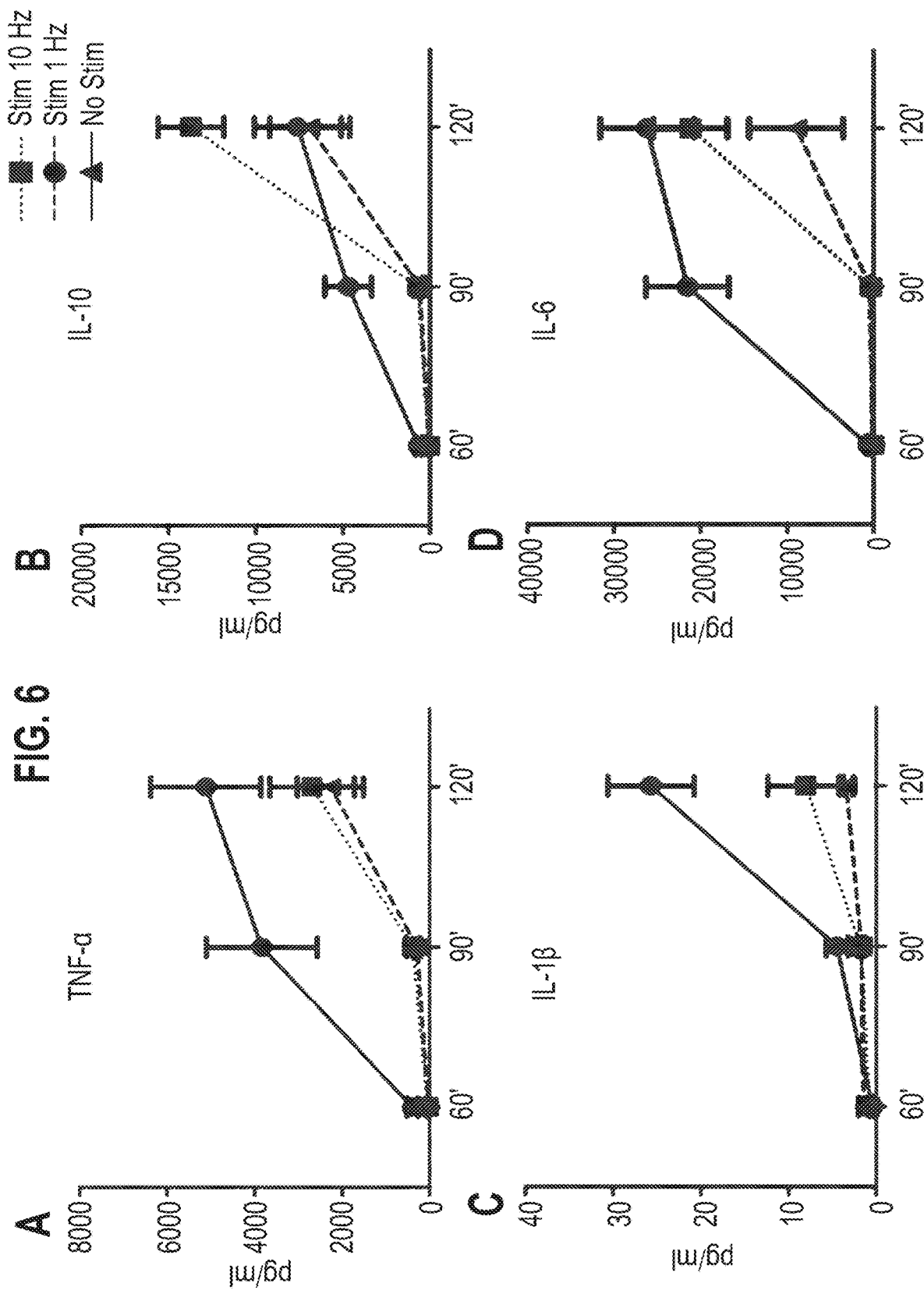

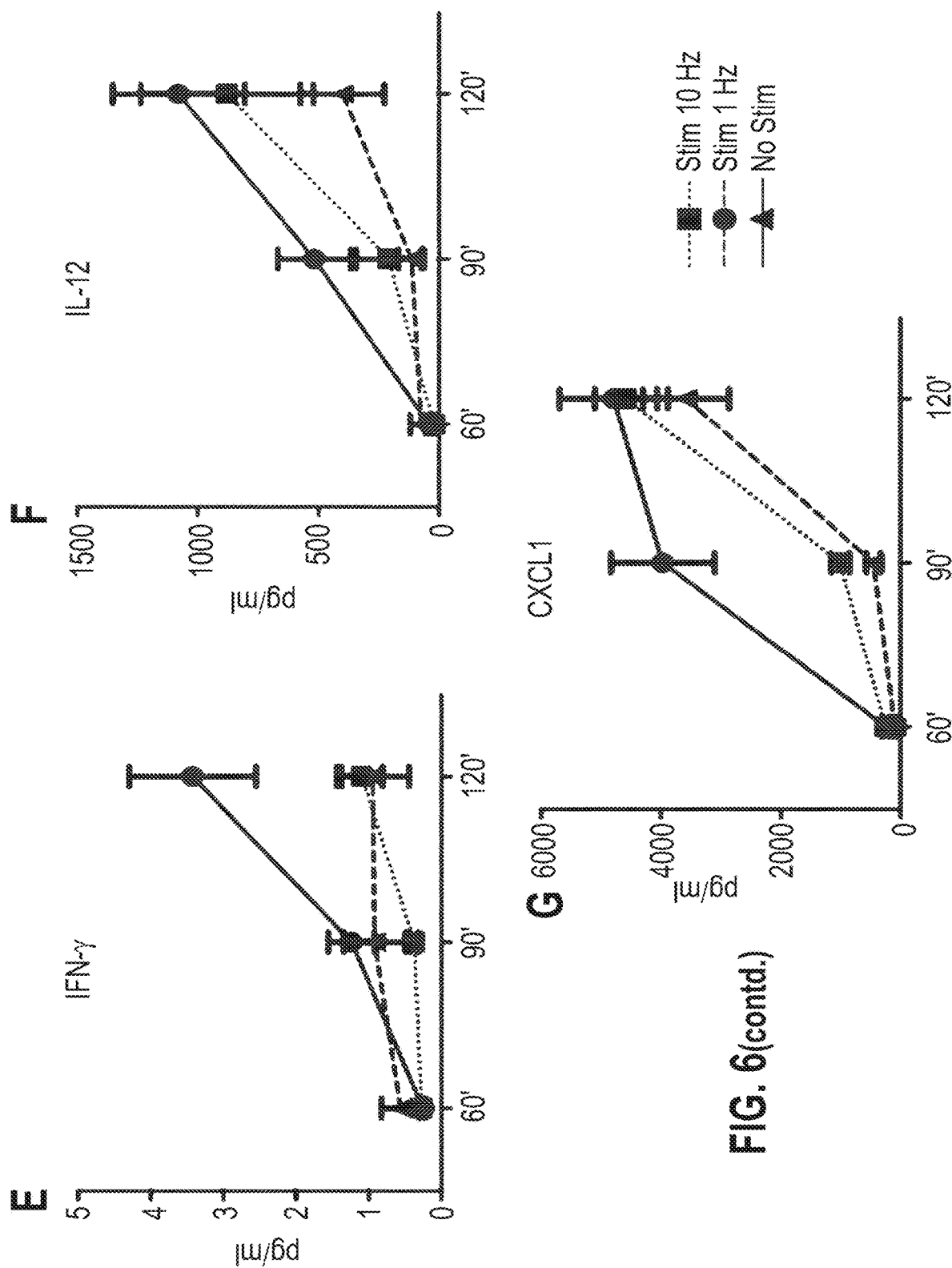
FIG. 6(contd.)

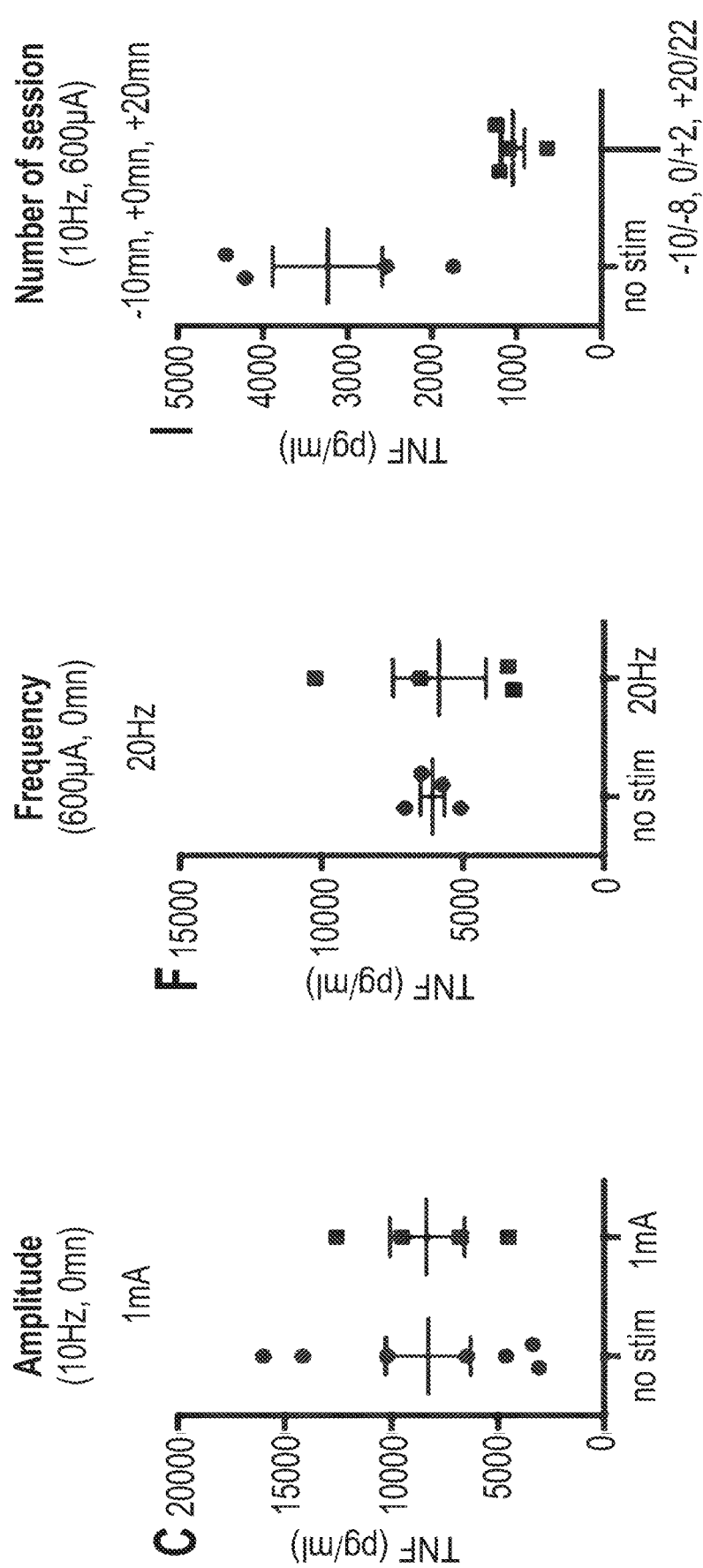
FIG. 7(contd.)

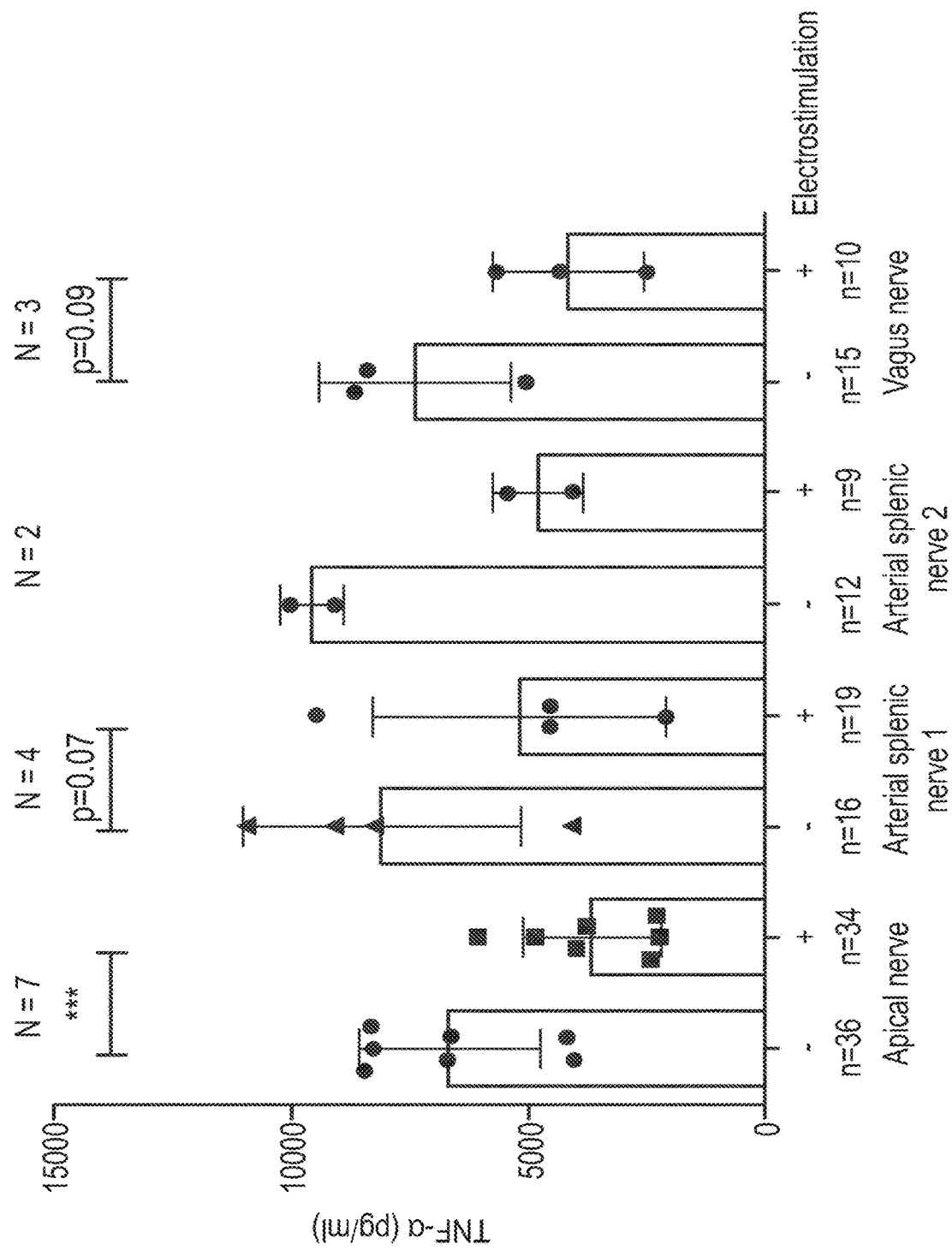

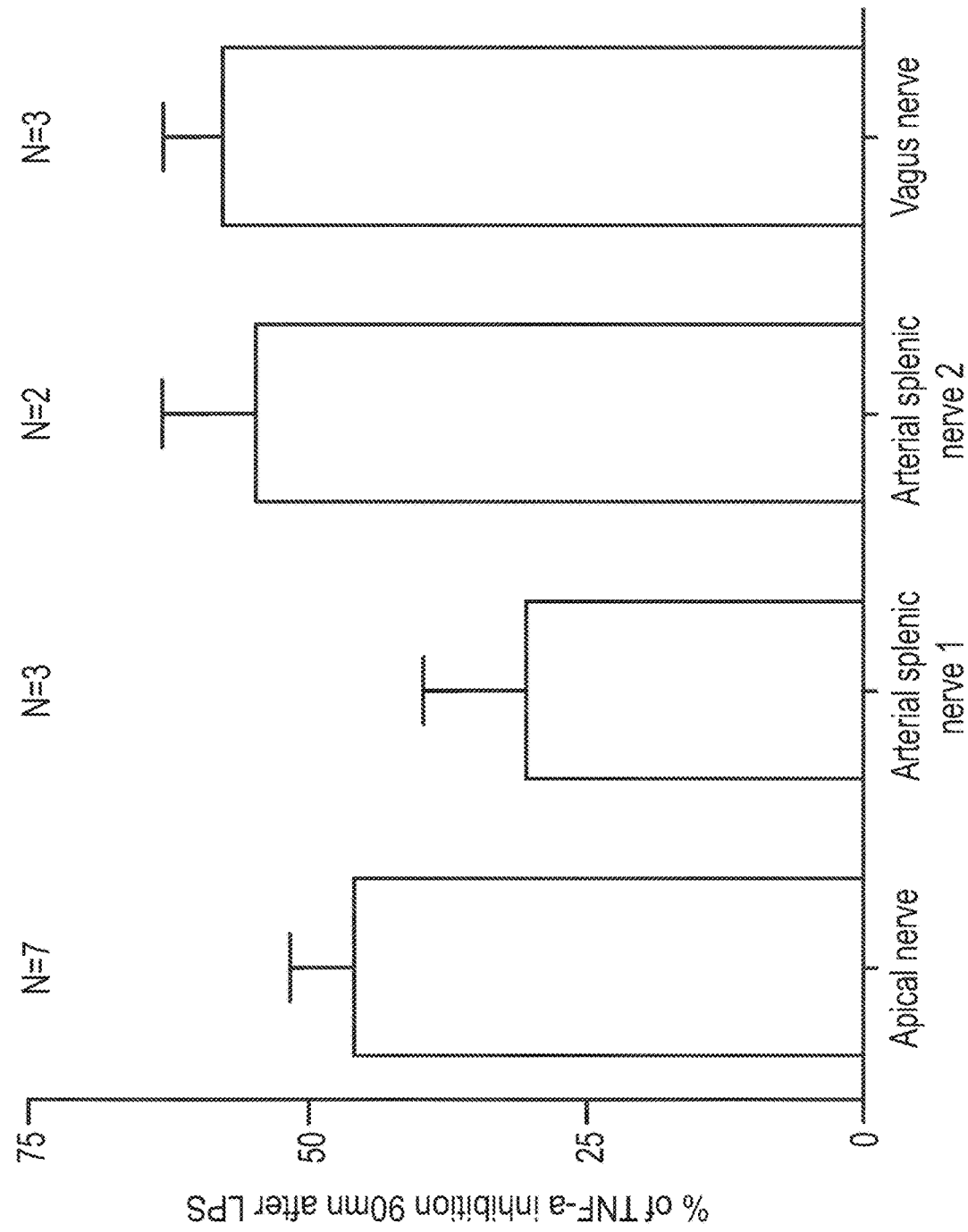

TREATMENT OF INFLAMMATORY DISORDERS

TECHNICAL FIELD

This invention relates to the treatment of inflammatory disorders, more particularly to methods and medical devices that deliver electrostimulation therapy for such purposes.

BACKGROUND ART

Inflammation plays a fundamental role in host defenses and the progression of immune-mediated diseases (reviewed in [1]). The inflammatory response is initiated in response to an injury and/or an infection by chemical mediators (e.g. cytokines and prostaglandins) and inflammatory cells (e.g. leukocytes). A controlled inflammatory response is beneficial, for example, in the elimination of harmful agents and the initiation of the repair of damaged tissue providing protection against infection. However, the inflammatory response can become detrimental if dysregulated, leading to a variety of inflammatory disorders such as rheumatoid arthritis, osteoarthritis, asthma, allergies, septic shock syndrome, atherosclerosis, and inflammatory bowel disease, Crohn's disease, ulcerative colitis, and other clinical conditions mediated by chronic inflammation.

The spleen contains half of the body's monocyte population making this organ the main contributor in inflammation, in particular in response to endotoxemic shock [2] and, consequently, the target for septic shock therapy. This organ is known to be innervated by different nervous branches (reviewed in [3]). The parasympathetic innervation of the spleen is a matter of debate since Dale's isolation of acetylcholine (ACh) from the spleen [3]. Buij and co-workers have suggested a parasympathetic innervation of the spleen in rodents [4, 5], but human correlation to this nerve is not known. The traditional view of splenic nerve is one of periarterial plexus which is proposed to be 98% sympathetic as demonstrated by neuroanatomical and neurochemical evidences [3].

From a functional point of view, vagus nerve stimulation (reviewed in [6]) as well as splenic nerve electrical stimulation inhibits LPS-induced TNF release in mice [7]. According to Tracey and coworkers, the splenic nerve activity is directly controlled by the cholinergic anti-inflammatory pathway (CAP) originating from the efferent branch of the vagus [6]. While vagal regulation of inflammatory tone and inflammatory reflex has received much attention, others have disputed the connections between vagus and splenic nerve. Some authors have shown that denervation of the arteriolar splenic nerve in mice led to the inhibition of the CAP [7]. However, Martelli et al. have challenged this view by showing that the splenic nerve was not directly connected to the vagus [8] but rather emerged as an independent branch of the greater splanchic nerve which controls splenic nerve activity [9, 10]. These authors also counter the view that neural sensing of inflammatory markers is humoral and not neural [11]. Furthermore, it is disputed whether the efferent arm of the inflammatory reflex response is sympathetic or parasympathetic.

Electrostimulation of the vagus nerve has been shown to relieve symptoms of rheumatoid arthritis in a clinical trial [12]. However, there are concerns that stimulation of the vagus nerve can produce undesired, non-specific CNS effects because the vagus nerve is comprised predominantly of afferent fibers and innervates other tissues in addition to the spleen, including the heart, liver and gastrointestinal tract.

References 7, 13, 14, 15 describe electrostimulation of the nerve plexus surrounding the splenic artery. However, this approach is not ideal because it may cause off-target effects. For example, it may cause arterial smooth muscle contraction through direct electrical stimulation or via activation of the network of arterial plexus nerves, and this may lead to an increased atherosclerotic risk in the area targeted. Furthermore, the splenic artery contains multiple pancreatic branches (including a great pancreatic artery or arteria magna pancreatica) that supply the pancreatic body and tail. Thus, stimulation of the nerve plexus surrounding the splenic artery may additionally lead to pancreatic stimulation.

Thus, there is a need for further and improved ways of treating inflammatory disorders, including autoimmune disorders (e.g. rheumatoid arthritis, osteoarthritis, psoriatic arthritis, spondyloarthropathy, ankylosing spondylitis, psoriasis, lupus, multiple sclerosis, Inflammatory Bowel Disease, Crohn's disease, and ulcerative colitis) and sepsis.

SUMMARY OF THE INVENTION

The inventors found that electrostimulation of a splenic nerve entering the superior pole of the spleen, referred to herein as an apical splenic nerve, is capable of modulating the levels of pro- and anti-inflammatory molecules, thereby reducing inflammation. More specifically, the inventors found that reversible electrostimulation of an apical splenic nerve is capable of decreasing pro-inflammatory cytokine levels and increasing LPS-induced anti-inflammatory cytokine levels, whilst causing minimal impact on basal body functions, such as arterial pressure and heart rate. Therefore, electrostimulation of an apical splenic nerve is effective in treating inflammatory disorders (e.g. autoimmune disorders, such as rheumatoid arthritis, osteoarthritis, psoriatic arthritis, spondyloarthropathy, ankylosing spondylitis, psoriasis, lupus, multiple sclerosis, Inflammatory Bowel Disease, Crohn's disease, and ulcerative colitis; and sepsis) by restoring the homeostatic balance of pro- and anti-inflammatory cytokines.

Thus, the invention provides a method of reducing inflammation in a subject by reversibly stimulating neural activity of an apical splenic nerve. A preferred way of reversibly stimulating the activity of an apical splenic nerve uses a device or system which applies a signal to the apical splenic nerve.

The invention also provides a method of reducing inflammation in a subject, comprising applying a signal to an apical splenic nerve to reversibly simulate the neural activity of the apical splenic nerve.

The invention provides a device or system for reversibly stimulating the neural activity of an apical splenic nerve in a subject, the device or system comprising: at least one transducer suitable for placement on or around the apical splenic nerve, and a signal generator for generating at least one signal to be applied to the apical splenic nerve via the at least one transducer such that the at least one signal stimulates the neural activity of the apical splenic nerve to produce a physiological response in the subject, wherein the physiological response is one or more of the group consisting of: a reduction in pro-inflammatory cytokines, an increase in anti-inflammatory cytokines, an increase in catecholamines, changes in immune cell population or immune cell surface co-stimulatory molecules, a reduction in factors involved in the inflammation cascade and/or a reduction in immune response mediators, wherein the at least one transducer is at least one electrode, and the signal generator is a voltage or current source configured to generate an electrical signal to be applied to the apical splenic nerve via the at least one electrode, and wherein the electrical signal has a frequency of between 1 Hz and 10 Hz.

The invention also provides a method of treating in a subject who suffers from, or is at risk of, an inflammatory disorder, comprising (i) implanting in the subject a device or system of the invention; positioning the transducer in signalling contact with an apical splenic nerve; and optionally (iii) activating the device or system.

Similarly, the invention provides a method of reducing inflammation in a subject, comprising: (i) implanting in the subject a device or system of the invention; (ii) positioning the transducer of the device or system in signalling contact with an apical splenic nerve; and optionally (iii) activating the device or system.

The invention also provides a method of implanting a device or a system of the invention in a subject, comprising: positioning a transducer of the device or system in signalling contact with an apical splenic nerve.

The invention also provides a device or a system of the invention, wherein the device or system is attached to an apical splenic nerve.

The invention further provides a neurostimulatory electrical waveform for use in reducing inflammation in a subject, wherein the waveform is comprised of a one or more pulse trains of square or sawtooth pulses, preferably biphasic pulses, the one or more pulse trains comprising pulses delivered at a frequency of between 1 Hz and 50 Hz, such that when applied to a subject's apical splenic nerve, the waveform stimulates neural activity in the apical splenic nerve.

The invention also provides the use of a stimulatory device or system for reducing inflammation in a subject, by reversibly stimulating neural activity in an apical splenic nerve.

The invention also provides a charged particle for use in a method of treating a subject who suffers from, or is at risk of, an inflammatory disorder, wherein the charged particle causes reversible depolarisation or hyperpolarization of the nerve membrane of an apical splenic nerve, such that an action potential is generated de novo in the modified nerve.

The invention also provides a modified apical splenic nerve to which a transducer of the system or device of the invention is attached. The transducer is in signalling contact with the nerve and so the nerve can be distinguished from the nerve in its natural state. Furthermore, the nerve is located in a subject who suffers from, or is at risk of, an inflammatory disorder.

The invention also provides a modified apical splenic nerve, wherein the neural activity is reversibly stimulated by applying a signal to the apical splenic nerve.

The invention also provides a modified apical splenic nerve, wherein the nerve membrane at the splenic nerve is reversibly depolarised or hyperpolarised by an electric field, such that an action potential is generated de novo in the modified nerve.

The invention also provides a modified apical splenic nerve bounded by a nerve membrane, comprising a distribution of potassium and sodium ions movable across the nerve membrane to alter the electrical membrane potential of the nerve so as to propagate an action potential along the nerve in a normal state; wherein at least a portion of the apical splenic nerve is subject to the application of a temporary external electrical field which modifies the concentration of potassium and sodium ions within the nerve, causing depolarization or hyperpolarization of the nerve membrane, thereby, in a disrupted state, temporarily generating an action potential de novo across that portion; wherein the nerve returns to its normal state once the external electrical field is removed.

The invention also provides a modified apical splenic nerve obtainable by reversibly stimulating neural activity of an apical splenic nerve according to a method of the invention.

The invention also provides a method of stimulating the activity of an apical splenic nerve, comprising a step of applying a signal to an apical splenic nerve in order to reversibly stimulate the neural activity of the apical splenic nerve in a subject. Preferably the method does not involve a method for treatment of the human or animal body by surgery. The subject already carries a device or system of the invention which is in signalling contact with the apical splenic nerve.

The invention also provides a method of controlling a device or system of the invention which is in signalling contact with an apical splenic nerve, comprising a step of sending control instructions to the device or system, in response to which the device or system applies a signal to the apical splenic nerve.

DETAILED DESCRIPTION OF THE INVENTION

The Splenic Nerves

Innervation of the spleen is primarily sympathetic or noradrenergic, with peptide neurons likely representing the bulk of the remaining neurons. The main sympathetic input to the spleen is derived from the celiac ganglion with postsynaptic fibers giving rise to the splenic plexus. The splenic plexus travels with the splenic artery to the spleen.

The splenic artery typically originates from the celiac plexus, courses anterior to the left kidney and left suprarenal gland, and runs in the splenorenal ligament behind or above the tail of the pancreas. In its course, it gives off numerous branches to the pancreas (dorsal pancreatic, greater pancreatic artery, and arteries to the tail) and, near its termination, it gives off the short gastric arteries and the left gastroepiploic artery.

En route to the spleen the nerve plexus accompanies the splenic artery and numerous branches. Nerve fibres are sent to the pancreas that appear to be involved in the regulation of islet function and thus glucose metabolism.

Vagal fibers that travel along the splenic artery have been described, and enter the pancreas where they synapse. The role of the more peripheral vagal fibers, in splenic function, is unclear.

In addition to the plexus nerves associated with the arterial vasculature, in rodents and some larger animal species, a nerve entering the superior pole of the spleen has been observed; and this nerve is referred to herein as the apical splenic nerve [16]. In cadaveric dissections in humans, this discrete nerve has been observed of approximately 1 mm diameter. The proximal origin has not yet been traced but the nerve may originate from the phrenic nerve or the Celiac ganglion, following inferior phrenic artery and then descending through the double fold of peritoneum that connects the thoracic diaphragm to the spleen, the phrenicosplenic ligament.

An apical splenic nerve naturally stimulates the spleen to produce anti-inflammatory effects by decreasing the production and secretion of pro-inflammatory cytokines, and increasing the production and secretion of anti-inflammatory cytokines. The inventors have shown that these effects are mediated by the norepinephrine released from the apical splenic nerve terminals. While not wishing to be bound by theory, it is postulated that norepinephrine interacts with the β-adrenergic receptors on the macrophages in the spleen, leading to decreased pro-inflammatory cytokines production and release, and/or increased anti-inflammatory cytokines production and secretion.

Thus, by stimulating neural activity in an apical splenic nerve, it is possible to modulate the levels of pro- and anti-inflammatory molecules (e.g. cytokines) to achieve therapeutic effects, such as reducing inflammation. In particular, stimulation of an apical splenic nerve decreases the production and secretion of pro-inflammatory cytokines, and increases the production and secretion of anti-inflammatory cytokines, thereby assisting in treating conditions associated with an imbalanced pro- and anti-inflammatory cytokine profile, e.g. inflammatory disorders.

Stimulation of an apical splenic nerve is more advantageous than stimulation of the nerve plexus surrounding the splenic artery, e.g. the periarteriolar branches of the splenic nerve (as described in 7, 13, 14, 15). This is because the apical splenic nerve is a discrete and a terminal branch. Thus, stimulation of an apical nerve to affect splenic function would avoid potential complications associated with direct arterial and pancreatic modulations compared to the periarteriolar branches of the splenic nerve.

Stimulation of the Splenic Nerve

According to the invention, stimulation results in neural activity in at least part of an apical splenic nerve being increased compared to baseline neural activity in that part of the nerve. This increase in activity can be across the whole nerve, in which case neural activity is increased across the whole nerve. Thus stimulation may apply to both afferent and efferent fibers of an apical splenic nerve, but in some embodiments modulation may apply only to afferent fibers or only to efferent fibers. Preferably, the stimulation applies to efferent fibers.

As used herein, "neural activity" of a nerve means the signalling activity of the nerve, for example the amplitude, frequency and/or pattern of action potentials in the nerve. The term "pattern", as used herein in the context of action potentials in the nerve, is intended to include one or more of: local field potential(s), compound action potential(s), aggregate action potential(s), and also magnitudes, frequencies, areas under the curve and other patterns of action potentials in the nerve or sub-groups (e.g. fascicules) of neurons therein.

Stimulation of neural activity, as used herein, is taken to mean that the signalling activity of the nerve is increased from the baseline neural activity—that is, the signalling activity of the nerve in the subject prior to any intervention. For example, stimulation typically involves increasing neural activity e.g. generating action potentials beyond the point of the stimulation in at least a part of an apical splenic nerve.

At any point along the axon, a functioning nerve will have a distribution of potassium and sodium ions across the nerve membrane. The distribution at one point along the axon determines the electrical membrane potential of the axon at that point, which in turn influences the distribution of potassium and sodium ions at an adjacent point, which in turn determines the electrical membrane potential of the axon at that point, and so on. This is a nerve operating in is normal state, wherein action potentials propagate from point to adjacent point along the axon, and which can be observed using conventional experimentation.

One way of characterizing a stimulation of neural activity is a distribution of potassium and sodium ions at one or more points in the axon which is created not by virtue of the electrical membrane potential at adjacent a point or points of the nerve as a result of a propagating action potential, but by virtue of the application of a temporary external electrical field. The temporary external electrical field artificially modifies the distribution of potassium and sodium ions within a point in the nerve, causing depolarization or hyperpolarization of the nerve membrane that would not otherwise occur. The depolarization or hyperpolarization of the nerve membrane caused by the temporary external electrical field generates de novo action potential across that point. This is a nerve operating in a disrupted state, which can be observed by a distribution of potassium and sodium ions at a point in the axon (the point which has been stimulated) that has an electrical membrane potential that is not influenced or determined by a the electrical membrane potential of an adjacent point.

Stimulation of neural activity is thus understood to be increasing neural activity from continuing past the point of stimulation. Thus, the nerve at the point of stimulation is modified in that the nerve membrane is reversibly deploarised or hyperpolarised by an electric field, such that a de novo action potential is generated and propagates through the modified nerve. Hence, the nerve at the point of stimulation is modified in that a de novo action potential is generated.

When an electrical signal is used with the invention, the stimulation is based on the influence of electrical currents (e.g. charged particles, which may be one or more electrons in an electrode attached to the nerve, or one or more ions outside the nerve or within the nerve, for instance) on the distribution of ions across the nerve membrane.

Stimulation of neural activity encompasses full stimulation of neural activity in the nerve—that is, embodiments where the total neural activity is increased in the whole nerve.

Stimulation of neural activity may be partial stimulation. Partial stimulation may be such that the total signalling activity of the whole nerve is partially increased, or that the total signalling activity of a subset of nerve fibres of the nerve is fully increased, or that the total signalling of a subset of nerve fibres of the nerve is partially increased compared to baseline neural activity in that subset of fibres of the nerve. For example an increase in neural activity of 5%, 10%, 15%, 20%, 25%, 30%, 35%, 40%, 45%, 50%, 60%, 70%, 80%, 90% or 95%, or an increase of neural activity in a subset of nerve fibres of the nerve. The neural activity may be measured by methods known in the art, for example, by the number of action potentials which propagate through the axon and/or the amplitude of the local field potential reflecting the summed activity of the action potentials.

The invention may selectively stimulate nerve fibres of various sizes within a nerve. Larger nerve fibres tend to have a lower threshold for stimulation than smaller nerve fibres. Thus, for example, increasing signal amplitude (e.g. increasing amplitude of an electric signal) may generate stimulation of the smaller fibres as well as larger fibers. For example, asymmetrical (triangular instead of square pulse) waveforms may be used stimulate C-fiber (unmyelinated).

One advantage of the invention is that stimulation of the neural activity is reversible. Hence, the stimulation of neural activity (an increase of neural activity versus baseline activity) is not permanent. That is, upon cessation of the signal, neural activity in the nerve returns substantially towards baseline neural activity within 1-60 seconds, or within 1-60 minutes, or within 1-24 hours (e.g. within 1-12 hours, 1-6 hours, 1-4 hours, 1-2 hours), or within 1-7 days (e.g. 1-4 days, 1-2 days). In some instances of reversible modulation, the neural activity returns substantially fully to baseline neural activity. That is, the neural activity following cessation of the signal is substantially the same as the neural activity prior to the modulation (i.e. prior to the signal being applied). Hence, the nerve or the portion of the nerve has regained its capacity to propagate action potentials.

In other embodiments, stimulation of the neural activity may be substantially persistent. As used herein, "persistent" is taken to mean that the stimulated neural activity has a prolonged effect. That is, upon cessation of the signal, neural activity in the nerve remains substantially the same as when signal was being applied—i.e. the neural activity during and following stimulation is substantially the same. Reversible stimulation is preferred.

Inflammatory Disorders

The invention is useful for treating conditions associated with an imbalance of pro- and anti-inflammatory cytokine profiles compared to the physiological homeostatic state.

Inflammatory disorders are typically characterized by an imbalance of pro- and anti-inflammatory cytokine profiles compared to the normal physiological homeostatic state, e.g. increased pro-inflammatory cytokines levels and/or decreased anti-inflammatory cytokines levels compared to the normal physiological homeostatic state.

Thus, the invention is useful for treating subjects suffering from, or are at risk in developing, inflammatory disorders. The invention may treat or ameliorate the effects of the inflammatory disorders by reducing inflammation. This may be achieved by decreasing the production and release of pro-inflammatory cytokines, and/or increasing the production and release of anti-inflammatory cytokines, from the spleen by reversibly electrically stimulating an apical splenic nerve.

Inflammatory disorders include autoimmune disorders, such as arthritis (e.g. rheumatoid arthritis, osteoarthritis, psoriatic arthritis), myasthenia gravis, thryoiditis, systemic lupus erythematosus, Goodpasture's syndrome, Behcets's syndrome, allograft rejection, graft-versus-host disease, Type I diabetes, ankylosing spondylitis, Berger's disease, diabetes including Type I diabetes, ankylosing spondylitis, Berger's disease, Retier's syndrome, spondyloarthropathy, ankylosing spondylitis, psoriasis, lupus, multiple sclerosis, Inflammatory Bowel Disease, Crohn's disease, and ulcerative colitis.

Further examples of inflammatory disorders include diseases involving the gastrointestinal tract and associated tissues, such as appendicitis, peptic, gastric and duodenal ulcers, peritonitis, pancreatitis, ulcerative, pseudomembranous, acute and ischemic colitis, inflammatory bowel disease, diverticulitis, epiglottitis, achalasia, cholangitis, coeliac disease, cholecystitis, hepatitis, Crohn's disease, enteritis, and Whipple's disease.

Further examples of inflammatory disorders include diseases of the bones, joints, muscles and connective tissues, such as the various arthritides and arthralgias, osteomyelitis, fasciitis, Paget's disease, gout, periodontal disease, rheumatoid arthritis, spondyloarthropathy, ankylosing spondylitis and synovitis.

Further examples include systemic or local inflammatory diseases and conditions, such as asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, and sarcoidosis.

Other examples include diseases involving the urogential system and associated tissues, such as septic abortion, epididymitis, vaginitis, prostatitis and urethritis, or diseases involving the respiratory system and associated tissues, such as bronchitis, emphysema, rhinitis, cystic fibrosis, adult respiratory distress syndrome, pneumonitis, pneumoultramicroscopicsilicovolcanoconiosis, alvealitis, bronchiolitis, pharyngitis, pleurisy, and sinusitis.

Further examples are diseases arising from infection by various viruses (such as influenza, respiratory syncytial virus, HIV, hepatitis B virus, hepatitis C virus and herpes), bacteria (such as disseminated bacteremia, Dengue fever), fungi (such as candidiasis) and protozoal and multicellular parasites (such as malaria, filariasis, amebiasis, and hydatid cysts).

Further examples are dermatological diseases and conditions of the skin (such as burns, dermatitis, dermatomyositis, sunburn, urticaria warts, and wheals); diseases involving the cardiovascular system and associated tissues (such as vasulitis, angiitis, endocarditis, arteritis, atherosclerosis, thrombophlebitis, pericarditis, myocarditis, myocardial ischemia, congestive heart failure, periarteritis nodosa, and rheumatic fever); as well as various cancers, tumors and proliferative disorders (such as Hodgkins disease), nosicomal infection; and, in any case the inflammatory or immune host response to any primary disease.

Other examples of inflammatory disorders include diseases involving the central or peripheral nervous system and associated tissues, such as Alzheimer's disease, meningitis, encephalitis, multiple sclerosis, cerebral infarction, cerebral embolism, Guillame-Barre syndrome, neuritis, neuralgia, spinal cord injury, paralysis, and uveitis.

Inflammatory disorders also include conditions associated with immune or inflammatory response include injury to nerves or other tissue and pain associated with nerve or other tissue. Injury may be due to a physical, chemical or mechanical trauma. Non-limiting examples of injury include acute trauma, burn, and whiplash. Conditions associated with a particular organ such as eye or ear may also include an immune or inflammatory response.

Preferably the invention is useful in treating autoimmune disorders, such as rheumatoid arthritis, osteoarthritis, psoriatic arthritis, spondyloarthropathy, ankylosing spondylitis, psoriasis, lupus, multiple sclerosis, Inflammatory Bowel Disease, Crohn's disease, and ulcerative colitis.

Treatment of the inflammatory disorder can be assessed in various ways, but typically involves an improvement in one or more detected physiological parameters. As used herein, an "improvement in a measurable physiological parameter" is taken to mean that, for any given physiological parameter, an improvement is a change in the value of that parameter in the subject towards the normal value or normal range for that value—i.e. towards the expected value in a healthy individual. For an example, in a subject having an inflammatory disorder, an improvement in a measurable parameter may (depending on which abnormal values a subject is exhibiting) be one or more of the group consisting of: a reduction in pro-inflammatory cytokines, an increase in anti-inflammatory cytokines, an increase in catecholamines (e.g. norepinephrine or epinephrine), changes in immune cell population or immune cell surface co-stimulatory molecules, a reduction in factors involved in the inflammation cascade and/or a reduction in immune response mediators. The invention might not lead to a change in all of these parameters.

By stimulating an apical splenic nerve, the spleen may: (a) decrease the secretion of a pro-inflammatory cytokine compared to baseline secretion; and/or (b) increase the secretion of an anti-inflammatory cytokine compared to baseline secretion. For example, the decrease in a pro-inflammatory cytokine secretion may be by: 5%, 10%, 15%, 20%, 25%, 30%, 35%, 40%, 45%, 50%, 60%, 70%, 80%, 90% or 95%. The increase in an anti-inflammatory cytokine secretion may be by: 5%, 10%, 15%, 20%, 25%, 30%, 35%, 40%, 45%, 50%, 60%, 70%, 80%, 90%, 95%, 100%, 150% or 200%.

Once the cytokine is secreted into the circulation, its concentration in circulation is diluted. Stimulation of an apical splenic nerve may result in: (a) a decrease in the concentration of a pro-inflammatory cytokine in circulation by 5%, 10%, 15%, 20%, 25%, 30%, 35%, 40%, 45%, 50%, 60%, 70%, 80%, 90%, or 95%; and/or (b) an increase in the concentration of an anti-inflammatory cytokine in circulation by 5%, 10%, 15%, 20%, 25%, 30%, 35%, 40%, 45%, 50%, 60%, 70%, 80%, 90%, 95%, 100%, 150% or 200%.

By stimulating an apical splenic nerve, the level of catecholamine (e.g. norepinephrine or epinephrine), e.g. its level in the spleen in the spleen, may increase, for example, by: 5%, 10%, 15%, 20%, 25%, 30%, 35%, 40%, 45%, 50%, 60%, 70%, 80%, 90%, 95%, 100%, 150% or 200%.

For example, the inventors found that stimulating an apical splenic nerve can decrease the concentration of a pro-inflammatory cytokine in the serum by at least ~50% (see FIG. 6; TNFα, IL-12, IL-1β, CXCL1, IL-6). The inventors also found that stimulating an apical splenic nerve can increase the concentration of an anti-inflammatory cytokine in the serum by at least ~50% (see FIG. 6; IL-10).

Pro-inflammatory cytokines are known in the art. Examples of these include tumor necrosis factor (TNF; also known as TNFα or cachectin), interleukin (IL)-1α, IL-1β, IL-2; IL-5, IL-6, IL-8, IL-15, IL-18, interferon γ (IFN-γ); platelet-activating factor (PAF), thromboxane; soluble adhesion molecules; vasoactive neuropeptides; phospholipase A2; plasminogen activator inhibitor (PAI-1); free radical generation; neopterin; CD14; prostacyclin; neutrophil elastase; protein kinase; monocyte chemotactic proteins 1 and 2 (MCP-1, MCP-2); macrophage migration inhibitory factor (MIF), high mobility group box protein 1 (HMGB-1), and other known factors.

Anti-inflammatory cytokines are also known in the art. Examples of these include IL-4, IL-10, IL-17, IL-13, IL-1α, and TNFα receptor.

It will be recognized that some of pro-inflammatory cytokines may act as anti-inflammatory cytokines in certain circumstances, and vice-versa. Such cytokines are typically referred to as plieotropic cytokines.

Factors involved in immune responses may be useful measurable parameters for the invention, for example, TGF, PDGF, VEGF, EGF, FGF, I-CAM, nitric oxide.

Chemokines may also be useful measurable parameters for the invention, such as 6cKine and MIP3beta, and chemokine receptors, including CCR7 receptor.

Changes in immune cell population (upregulated Langerhans cells, dendritic cells, lymphocytes), or immune cell surface co-stimulatory molecules (Major Histocompatibility, CD80, CD86, CD28, CD40) may also be useful measurable parameters for the invention.

Factors involved in the inflammatory cascade may also be useful measurable parameters for the invention. For example, the signal transduction cascades include factors such as NFκ-B, Egr-1, Smads, toll-like receptors, and MAP kinases.

Methods of assessing these measurable parameters are known in the art. Detection of any of the measurable parameters may be done before, during and/or after modulation of neural activity in an apical splenic nerve.

For example, a cytokine, chemokine, or a catecholamine (e.g. norepinephrine or epinephrine) may be directly detected, e.g. by ELISA. Alternatively, the presence or amount of a nucleic acid, such as a polyribonucleotide, encoding a polypeptide described herein may serve as a measure of the presence or amount of the polypeptide. Thus, it will be understood that detecting the presence or amount of a polypeptide will include detecting the presence or amount of a polynucleotide encoding the polypeptide.

Quantitative changes of the biological molecules (e.g. cytokines) can be measured in a living body sample such as urine or plasma. Detection of the biological molecules may be performed directly on a sample taken from a subject, or the sample may be treated between being taken from a subject and being analysed. For example, a blood sample may be treated by adding anti-coagulants (e.g. EDTA), followed by removing cells and cellular debris, leaving plasma containing the relevant molecules (e.g. cytokines) for analysis. Alternatively, a blood sample may be allowed to coagulate, followed by removing cells and various clotting factors, leaving serum containing the relevant molecules (e.g. cytokines) for analysis.

As used herein, a physiological parameter is not affected by the stimulation of the apical splenic neural activity if the parameter does not change (in response to apical splenic nerve stimulation) from the average value of that parameter exhibited by the subject or subject when no intervention has been performed i.e. it does not depart from the baseline value for that parameter.

The skilled person will appreciate that the baseline for any physiological parameter in an individual need not be a fixed or specific value, but rather can fluctuate within a normal range or may be an average value with associated error and confidence intervals. Suitable methods for determining baseline values are well known to the skilled person.

As used herein, a measurable physiological parameter is detected in a subject when the value for that parameter exhibited by the subject at the time of detection is determined. A detector is any element able to make such a determination.

In certain embodiments, the invention further comprises a step of detecting one or more physiological parameters of the subject, wherein the signal is applied only when the detected physiological parameter meets or exceeds a predefined threshold value. The physiological parameter may be any parameter described herein.

Thus, in certain embodiments, the invention further comprises a step of detecting one or more physiological parameters of the subject, wherein the signal is applied only when the detected physiological parameter meets or exceeds a predefined threshold value. In such embodiments wherein more than one physiological parameter is detected, the signal may be applied when any one of the detected parameters meets or exceeds its threshold value, alternatively only when all of the detected parameters meet or exceed their threshold values. In certain embodiments wherein the signal is applied by a neurostimulatory device/system, the device/system further comprises at least one detector configured to detect the one or more physiological parameters.

In certain embodiments of the method, the one or more detected physiological parameters are one or more of the group consisting of: cytokine content, chemokine content, immune cell population content, immune cell surface co-stimulatory molecules content, inflammation cascade factor content and/or immune response mediator content.

A "predefined threshold value" for a physiological parameter is the minimum (or maximum) value for that parameter that must be exhibited by a subject or subject before the specified intervention is applied. For any given parameter, the threshold value may be defined as a value indicative of a pathological state or a disease state, or as a value indicative of the onset of a pathological state or a disease state. Thus, depending on the predefined threshold value, the invention can be used as a prevention or a treatment. Alternatively, the threshold value may be defined as a value indicative of a physiological state of the subject (that the subject is, for example, asleep, post-prandial, or exercising). Appropriate values for any given parameter would be simply determined by the skilled person (for example, with reference to medical standards of practice).

Such a threshold value for a given physiological parameter is exceeded if the value exhibited by the subject is beyond the threshold value—that is, the exhibited value is a greater departure from the normal or healthy value for that parameter than the predefined threshold value.

In certain embodiments of the method, the method does not affect one or more physiological parameters in the subject selected from the group consisting of: arterial blood pressure, heart rate, and glucose metabolism. Suitable methods for determining the value for any given parameter would be appreciated by the skilled person.

A subject of the invention may, in addition to having an implant, receive medicine for their condition. For instance, a subject having an implant according to the invention may receive an anti-inflammatory medicine (which will usually continue medication which was occurring before receiving the implant). Such medicines include, nonsteroidal anti-inflammatory drugs (NSAIDs), steroids, 5ASAs, immunosuppressants such as azathioprine, methotrexate and ciclosporin, and biological drugs like infliximab and adalimumab. Thus the invention provides the use of these medicines in combination with a device/system of the invention.

An Implantable Device/System for Implementing the Invention

An implantable device according to the invention comprises at least one transducer, preferably an electrode, suitable for placement on or around an apical splenic nerve. The device/system preferably also comprises a controller coupled to the at least one transducer. The various components are preferably part of a single physical device. As an alternative, however, the invention may use a system in which the components are physically separate, and communicate wirelessly. Thus, for instance, the transducer and the controller can be part of a unitary device, or together may form a system (and, in both cases, further components may also be present to form a larger device or system e.g. a power source, a sensor, etc.).

Electrodes

Electrodes capable of controlling delivery of current to a nerve cell in order to affect the signals passing along the nerve fiber are known in the art. Reference 17 discloses several types of electrode for non-damaging neural tissue conduction block. The document discloses cuff electrodes (e.g. spiral cuff, helical cuff or flat interface), and flat interface electrodes, both of which are also suitable for use with the present invention. A mesh, a linear rod-shaped lead, paddle-style lead or disc contact electrode (including multi-disc contact electrodes) are also disclosed in Reference 17 and would be suitable for use in the present invention. Also suitable are intrafascicular electrode, glass suction electrode, paddle electrode, bipolar hemi-cuff electrode, bipolar hook electrode, percutaneous cylindrical electrode. Electrodes may be monopolar, bipolar, tripolar, quadripolar or have five or more poles. The electrodes may fabricated from, or be partially or entirely coated with, a high charge capacity material such as platinum black, iridium oxide, titanium nitride, tantalum, poly(elthylenedioxythiophene) and suitable combinations thereof. A hook electrode, such as a hook electrode from Harvard Apparatus (Holliston, USA), is preferred for acute electrostimulation. A bipolar electrode, such as a bipolar electrode from Cortec (Freiburg, Germany), is preferred for chronic implantation.

In particular, a sling electrode is preferred, depending on the type of nerve. A sling electrode is preferred for attachment to an apical splenic nerve. For example, a sling electrode of 1 mm length and 100 µm diameter may be used to attach to an apical splenic nerve.

Reference 18 discloses separated-interface nerve electrodes, and in particular forms of ionic coupling electrodes (for example in the form of a cuff electrode) that facilitates the application of a prolonged single phase current to a nerve which mitigates the kind of nerve damage described elsewhere herein. This kind of electrode would be suitable for use in the present invention.

Similar disclosures concerning other neural modulation techniques, such as neural stimulation as well as neural inhibition or block are also known in the art, as described elsewhere herein.

Suitable Forms of an Electrical Signal

Signals applied according to the invention are ideally non-destructive. As used herein, a "non-destructive signal" is a signal that, when applied, does not irreversibly damage the underlying neural signal conduction ability of the nerve. That is, application of a non-destructive signal maintains the ability of an apical splenic nerve (or fibres thereof, or other nerve tissue to which the signal is applied) to conduct action potentials when application of the signal ceases, even if that conduction is in practice artificially modulated, such as stimulated, inhibited or blocked as a result of application of the non-destructive signal.

The signal will usually be an electrical signal, which may be, for example, a voltage or current waveform. As used herein, "charge-balanced" in relation to a DC current is taken to mean that the positive or negative charge introduced into any system (e.g. a nerve) as a result of a DC current being applied is balanced by the introduction of the opposite charge in order to achieve overall (net) neutrality. However, electrical signals are just one way of implementing the invention, and other suitable signals are described below.

In certain embodiments the DC waveform or AC waveform may be a square, sinusoidal, triangular or complex waveform. The DC waveform may alternatively be a constant amplitude waveform. In certain embodiments the electrical signal is an AC sinusoidal waveform. Preferably the waveform comprises one or more pulse trains, each comprising a plurality of charged-balanced biphasic pulses, each having a pulse width as described below. Waveforms of different amplitudes can be used. Amplitudes of between 200 µA and 5 mA can be used, preferably between 350 µA and 1 mA, preferably 600 µA or 650 µA. Frequencies of between 1 Hz and 50 Hz can be used, preferably between 2 Hz and 30 Hz, more preferably between 5 Hz and 20 Hz, most preferably 10 Hz. Pulse widths of different durations may be used. Durations of between 10 µs and 5 ms, preferably between 20 µs and 4 ms, more preferably between 50 µs and 2 ms, yet more preferably between 100 µs and 1 ms, yet more preferably between 200 µs and 500 µs. A 2 ms pulse width (including both positive and negative phases of the pulse, in the case of a charged-balanced biphasic pulse) has been used for the waveforms described in the examples above. In particular, the following signals have been used: 600 µA or 650 µA, 10 Hz, 2 ms pulse width; and 350 µA, 1 Hz or 10 Hz, 2 ms pulse width.

The electric signal may be applied as step change or as a ramp change in current or intensity.

It will be appreciated by the skilled person that the current amplitude of an applied electrical signal necessary to achieve the intended neurostimulation will depend upon the positioning of the electrode and the associated electrophysiological characteristics (e.g. impedance). It is within the ability of the skilled person to determine the appropriate current amplitude for achieving the intended neurostimulation in a given subject. For example, the skilled person is aware of methods suitable to monitor the neural activity profile induced by neuromodulation or neurostimulation.

Stimulation of an apical splenic nerve can be achieved using electrical signals which serve to replicate the normal neural activity of the apical splenic nerve. Preferred embodiments of the stimulating signal comprise a plurality of temporally separated pulse trains, each pulse train being made up of a plurality of pulses.

The signal generator may be configured to deliver the one or more pulse trains at intervals described below. The frequencies of the plurality of pulses may be between 1 Hz and 50 Hz (i.e. between 1 pulse per second and 10 pulses per second, within a given pulse train). Whilst frequencies of between 1 Hz and 50 Hz are possible, frequencies between 1 Hz and 30 Hz are expected to be more viable and frequencies between 1 Hz and 20 Hz ore viable still. Frequencies of 1 Hz, 5 Hz and particularly 10 Hz are preferred, though any frequency within the range may be chosen.

The signal generator may be configured to deliver pulses at a constant current of 600 µA or 650 µA, though the current may be between 200 µA and 5 mA, preferably between 350 µA and 1 mA.

The signal generator is configured to deliver a pulse train (comprising a plurality of pulses) for a period of 120 seconds (i.e. 2 minutes), though the duration may be between 30 seconds and 240 seconds, preferably between 60 seconds and 180 seconds.

Advantages have noted in respect of waveforms having pulses of shorter pulse widths and lower amplitudes. In particular waveforms with pulse widths between 200 µs and 500 µs and pulse amplitudes between 350 µA and 600 µA are preferred, though waveforms with pulse widths between 50 µs and 1 ms and pulse amplitudes between 200 µA and 650 µA are also advantageous.

The signal generator may be pre-programmed to deliver one or more pre-defined waveforms with parameters falling within the range given above. Alternatively, the signal generator may be controllable to adjust one or more of the parameters, namely pulse duration, pulse train frequency, pulse current amplitude, signal duration. Control may be open loop, wherein the user or operator of the implantable device may configure the signal generator using an external controller, or control may be closed loop, wherein signal generator modifies the signal parameters in response to sensed physiological signals.

Signal Timing

The preferred stimulation signal (i.e. pulse train), as described elsewhere herein, which may for example be of 2 minutes duration, may be applied ad-hoc or periodically. A preferred periodicity for the application of the signal is every 5 minutes, every 10 minutes or every 20 minutes, for a given length of time or indefinitely.

It is desirable to apply the preferred stimulation signal, again preferably of 2 minutes duration, concurrently with the onset of endotoxemic or septic shock, and/or after the onset of endotoxemic or septic shock. In particular it is desirable to apply the preferred stimulation signal at the time of onset of endotoxemic or septic shock and/or 5 minutes after the onset of endotoxemic or septic shock and/or 10 minutes after the onset of endotoxemic or septic shock and/or 20 minutes after the onset of endotoxemic or septic shock.

It is furthermore desirable to repeat the application of the above-described preferred stimulation signal one or more of 16, 20, 24, 30, 34 and 38 hours after the onset of endotoxemic or septic shock.

Microprocessor

The implantable device may comprise a microprocessor. The microprocessor may be responsible for triggering the beginning and/or end of the signals delivered to an apical splenic nerve by the at least one transducer. Optionally, the microprocessor may also be responsible for generating and/or controlling the parameters of the signal. A pulse generator with a processor configuration suitable for nerve stimulation applications is disclosed in ref. 14.

The microprocessor may be configured to operate in an open-loop fashion, wherein a pre-defined signal (e.g. as described above) is delivered to an apical splenic nerve at a given periodicity (or continuously) and for a given duration (or indefinitely) with or without an external trigger, and without any control or feedback mechanism. Alternatively, the microprocessor may be configured to operate in a closed-loop fashion, wherein a signal is applied based on a control or feedback mechanism. As described elsewhere herein, the external trigger may be an external controller operable by the user or operator to initiate delivery of a signal.

The microprocessor of the device may be constructed so as to generate, in use, a preconfigured and/or user-selectable signal that is independent of any input. Preferably, however, the microprocessor is responsive to an external signal, more preferably information pertaining to a physiological response in the subject.

The implantable device of the present invention may comprise circuitry to detect physiological signals indicative of the levels of signalling molecules secreted from the spleen, and use these signals to trigger the microprocessor to deliver a signal of the kinds described above to an apical splenic nerve using the at least one transducer. Upon receipt of signals received from the one or more sensors, the processor may calculate the current levels of signalling molecules secreted from the spleen in accordance with techniques known in the art.

The device may comprise memory for storing physiological data pertaining to normal levels of signalling molecules secreted from the spleen. The data may be specific to the patient into which the device is implanted, and gleaned from various tests known in the art. Upon receipt of signals received from the one or more sensors, or else periodically or upon demand, the processor may compare the signals received from the one or more sensors with the physiological data stored in the memory and determine whether the received signals are indicative of insufficient or excessive levels of signalling molecules secreted from the spleen. The device may be configured such that if and when an insufficient or excessive level of signalling molecules secreted from the spleen is indicated, the processor triggers delivery of a signal to an apical splenic nerve by the at least one transducer, in the manner described elsewhere herein. For instance, if a signal indicative of excessive TNF concentration in the circulation is detected, the processor may trigger delivery of a signal which dampens secretion of the respective signalling molecule, as described elsewhere herein.

As an alternative, or in addition, to the device's ability to respond to sensed physiological signals, the processor may be triggered upon receipt of a signal generated by a physician or by the subject in which the device is implanted. To that end, the implantable device may be part of a system comprising subsystems external to the subject, and including, for instance, a controller. An example of such a system is described below.

The controller may be configured to apply any one or more of the above signals to an apical splenic nerve intermittently or continuously. Intermittent application of a signal involves applying the signal in an (on-off)$_n$ pattern, where n>1. For instance, the signal can be applied continuously for at least 5 days, optionally at least 7 days, before ceasing for a period (e.g. 1 day, 2 days, 3 days, 1 week, 2 weeks, 1 month), before being again applied continuously for at least 5 days, etc. Thus the signal is applied for a first time period, then stopped for a second time period, then reapplied for a third time period, then stopped for a fourth time period, etc. In such an embodiment, the first, second, third and fourth periods run sequentially and consecutively. The duration of the first, second, third and fourth time periods is independently selected. That is, the duration of each time period may be the same or different to any of the other time periods. In certain such embodiments, the duration of each of the first, second, third and fourth time periods may be any time from 1 second (s) to 10 days (d), 2 s to 7 d, 3 s to 4 d, 5 s to 24 hours (24 h), 30 s to 12 h, 1 min to 12 h, 5 min to 8 h, 5 min to 6 h, 10 min to 6 h, 10 min to 4 h, 30 min to 4 h, 1 h to 4 h. In certain embodiments, the duration of each of the first, second, third and fourth time periods is 5 s, 10 s, 30 s, 60 s, 2 min, 5 min, 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 2 d, 3 d, 4 d, 5 d, 6 d, 7 d.

In certain embodiments, the signal is applied for a specific amount of time per day. In certain such embodiments, the signal is applied for 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day. In certain such embodiments, the signal is applied continuously for the specified amount of time. In certain alternative such embodiments, the signal may be applied discontinuously across the day, provided the total time of application amounts to the specified time.

Continuous application may continue indefinitely, e.g. permanently. Alternatively, the continuous application may be for a minimum period, for example the signal may be continuously applied for at least 5 days, or at least 7 days.

Where the signal is controlled by a device/system of the invention, and where a signal is continuously applied to the nerve, although the signal might be a series of pulses, the gaps between those pulses do not mean the signal is not continuously applied.

In certain embodiments, the signal is applied only when the subject is in a specific state e.g. only when the subject is awake, only when the subject is asleep, prior to and/or after the ingestion of food, prior to and/or after the subject undertakes exercise, etc.

These various embodiments for timing of inhibition can all be achieved using the controller in a device/system of the invention.

Other Components of the Implantable Device

The implantable device may be powered by a power source, which may comprise a current source and/or a voltage source for providing the power for the signal delivered to an apical splenic nerve by the at least one transducer. The power source may also provide power for the other components of the device, such as the microprocessor, memory and communication subsystem (described below). The power source may comprise a battery and may be rechargeable. It will be appreciated that the availability of power is limited in implantable devices, and the invention has been devised with this constraint in mind. The device/system may be powered by inductive powering or a rechargeable power source.

The implantable device may comprise a communication subsystem, for instance comprising a transceiver coupled to the processor. The transceiver may use any suitable signalling process such as RF, wireless, infrared and so on, for transmitting signals outside of the body, for instance to a system of which the implantable device is one part.

System Including Implantable Device

The implantable device of the invention may be part of a system that includes a number of subsystems. For instance, the system may comprise subsystems located outside of the body, including a subsystem for wirelessly recharging the battery used to power the implantable device, and a controller with a communications subsystem that is configured to communicate with the communications subsystem of the implantable device.

The controller may comprise an actuator which, upon being pressed by a physician or the subject for instance, will deliver a signal, via the respective communications subsystems, to trigger the processor of the implantable device to deliver a signal to an apical splenic nerve by the at least one transducer.

The controller may also be configured to make adjustments to the operation of the implantable device. For instance, it may transmit, via the respective communications subsystems, physiological data pertaining to a normal level of signalling molecules secreted from the spleen. The data may be specific to the patient into which the device is implanted. The controller may also be configured to make adjustments to the operation of the power source, signal generation and processing elements and/or electrodes in order to tune the signal current delivered to an apical splenic nerve by each node of an electrode, or by each electrode.

A device/system of the invention is preferably made from, or coated with, a biostable and biocompatible material. This means that the device/system is both protected from damage due to exposure to the body's tissues and also minimises the risk that the device/system elicits an unfavourable reaction by the host (which could ultimately lead to rejection). The material used to make or coat the device/system should ideally resist the formation of biofilms. Suitable materials include, but are not limited to, poly(p-xylylene) polymers (known as Parylenes) and polytetrafluoroethylene.

A device/system of the invention will generally weigh less than 50 g.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x+10%.

Unless otherwise indicated each embodiment as described herein may be combined with another embodiment as described herein.

BRIEF DESCRIPTION OF THE DRAWINGS

FIG. 5B shows the percentage of HR, mean BP, maximum BP (max BP) and minimum BP (min BP) in anaesthetized mice post-electrostimulation relative to pre-electrostimulation. The data were pooled from three independent mice. The apical splenic nerve or the vagus nerve was stimulated.

FIG. 6 shows various LPS-induced cytokine levels in serum compared between mice that had and had not been electrostimulated at the apical splenic nerve (n=5-6 animals/group). (A) TNF-α, (B) IL-10, (C) IL-1β, (D) IL-6, (E) IFN-γ, (F) IL-12, (G) CXCL1.

FIG. 8 shows the LPS-induced TNF levels in serum compared between conscious mice that had and had not been electrostimulated at apical or periarteriolar branches of the splenic nerve (arterial splenic nerve 1 or 2), or the vagus nerve. In FIG. 8A, the TNF levels (pg/ml) are indicated per group/mouse. Number of experiments (N) and total number of mice (n) are indicated, each group consisted of n=4-7 mice. FIG. 8B expresses the data in FIG. 8A as percent of inhibition of TNF compared to control mice.

MODES FOR CARRYING OUT THE INVENTION

Materials and Methods

Mice and Reagents

Figure 1A:
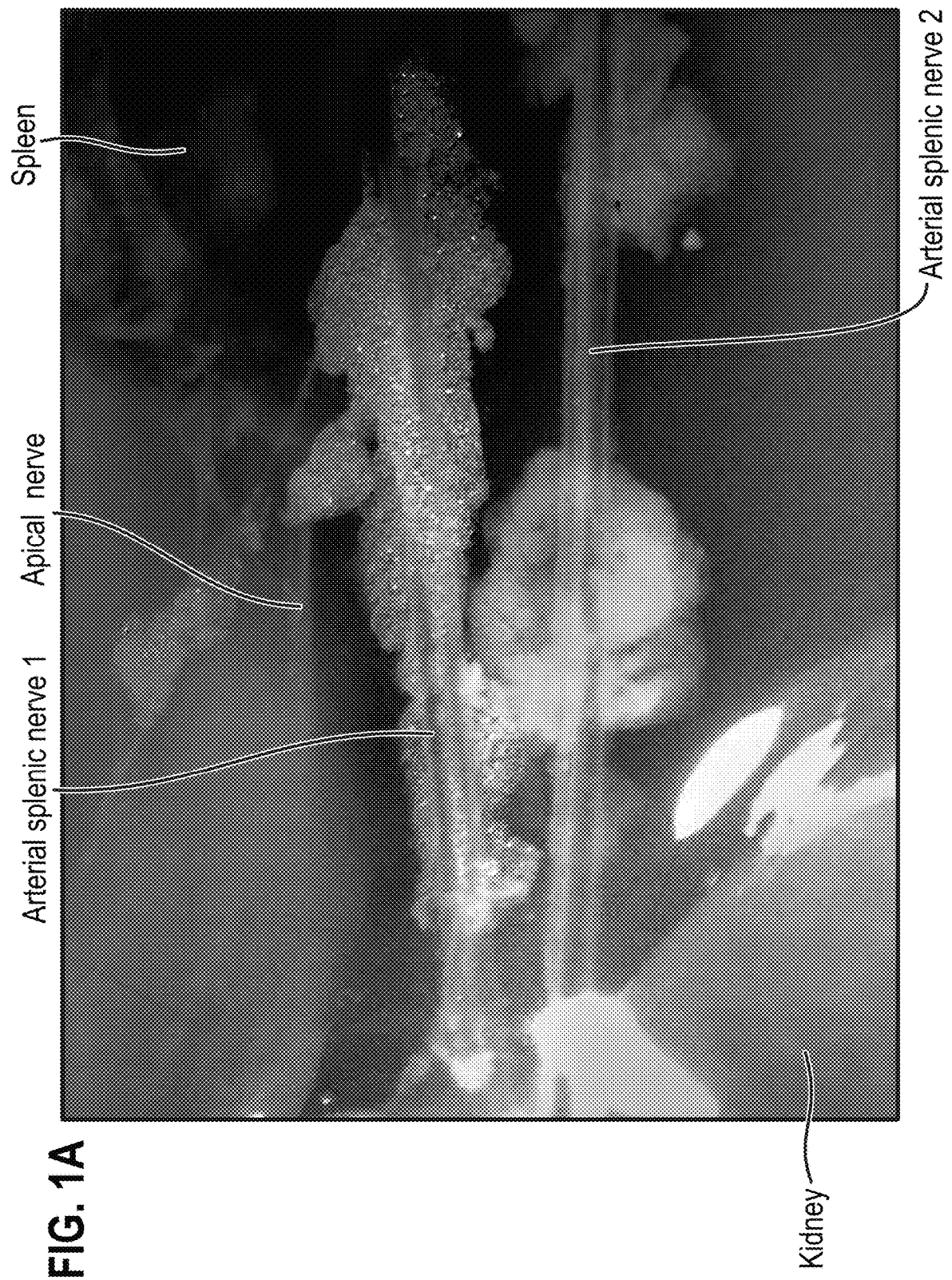
FIG. 1A shows a representative image of the nerves innervating the spleen in a mouse.

TH-Ires-Cre and Ai14 mice were used in the experiments. A sublethal (5 mg/kg) or lethal (20 mg/kg) dose of LPS from E. Coli 0127:B8 (Sigma Aldrich) was given intraperitoneally to the mice as indicated in the legend of the figures.

Electrodes

For acute electrostimulations, animals were anesthetized with a mixture of Ketamine (75 mg/kg) and Xylazine (60 mg/kg) i.p. The animal's trunk was shaved, the splenic nerve was exposed by a ventrolateral approach and the nerve was either cut or placed on a hook electrode from Harvard Apparatus (Holliston, USA). Animals were injected with a sublethal dose of LPS and kept anesthetized until blood sampling. Supplementary doses of anesthetic were given as needed to maintain anesthesia. For chronic implantation, animals were anesthetized by 2% isofluorane. The apical splenic nerve was exposed as described above and a bipolar electrode from Cortec (Freiburg, Germany) was implanted either onto the apical splenic (sling, 1 mm length, 100 μm diameter), the arterial splenic- (sling, 2 mm length, 100 μm diameter) or the vagus (tunnel, 2 mm length, 200 μm diameter) nerve. The wires were maintained in place by a stitch point placed on the abdominal muscles and exited abdominally. To avoid animal scraping, the abdomen was wrapped with bandages. The total duration of the procedure was about 20 minutes per animal. A morphinic derivative was given before and after the surgery (Buprecare®, 0.1 mg/kg, i.p. 30 minutes before surgery and 0.05 mg/kg, s.c. after surgery and the following 2 days). Five days later, animals were injected with a sublethal dose of LPS, electrostimulated and blood samples were collected 90 minutes later.

Electrostimulation

Electrostimulation was performed using a PlexStim V2.3 from Plexon (Dallas, Tex., USA). Unless specified, the set-up of the electrostimulation were rectangular charged-balanced biphasic pulses with 650 μA pulse amplitude, 2 ms pulse width (positive and negative) at 10 Hz frequency.

Detection of Norepinephrine, TNF and IL-6

Norepinephrine (NE) levels in biopsies were determined using a competitive ELISA for the quantitative determination of NE according to the manufactures protocol (DLD Diagnostika GmbH, Hamburg, Germany).

Tumor Necrosis factor (TNF) and interleukin 6 (IL-6) sera were diluted 10-fold with PBS, and cytokine concentrations were assessed in duplicate by ELISA (R&D DuoSet, Minneapolis, Minn., USA) according to the manufacturers protocol.

For multicytokine measurement (FIG. 6), the Meso Scale Discovery (MSD) multiplex assay kits (Rockville, Mass., USA) were used, and the kits allow quantitation of multiple analytes in the same sample with wide range of detection. V-PLEX Proinflammatory panel 1 mouse kit was used in this experiment.

Statistics

The student T-test or logrank test were used to calculate statistical differences. Mann-Whitney (FIG. 2) and Annova test were performed for small size groups. The survival curve gives a p=0.188 (LogRank test).

Blood Pressure Recording

Blood pressure was recorded on acutely electrostimulated animals by inserting a catheter into the common branch of the carotid. The catheter was connected to a blood pressure transducer TSD104A-MRI and to a data acquisition unit.

Septic Shock

Animals were operated as above-mentioned for chronic implantation. A lethal dose of LPS (400 µg/animal) was administered after five days recovery and electrostimulation (650 µA, 10 Hz, 2 ms pulse width) was applied for 2 minutes starting at −10, and +20 minutes relative to LPS challenge and again at 16, 20, 24, 30, 34 and 38 h post-LPS challenge for 2 min. Survival was monitored by three times daily examination of the cages.

Results

The Three Nerves that Project to the Mouse Spleen Contain Catecholaminergic Fibers Mice (n=4) were dissected to assess the anatomical organization of the splenic nerves, and FIG. 1A shows a representative image. It can be seen that the spleen is innervated by at least two distinct arteriolar associated nerves and a non-arteriolar associated nerve located at the apex of the spleen near the stomach. The latter is referred to as an apical splenic nerve.

It was then investigated whether the apical splenic nerve in mice was of catecholaminergic nature. A transgenic mouse strain was generated to express a fluorescent reporter (tdTomato+) in the catecholaminergic fibers. TH-Ires-Cre C57/B16 mice in which the site-specific Cre recombinase was selectively expressed in cells that express the Tyrosine Hydroxylase (TH) were crossed with Ai14 mice that carry a loxP-flanked STOP cassette that prevented transcription of the downstream red fluorescent protein variant (tdTomato) inserted into the Gt(ROSA)26Sor locus. Because TH was selectively expressed in catecholaminergic fibers, the STOP sequence was deleted and tdTomato expression was observed only in these cells in the double mutant offspring.

Figure 1B:
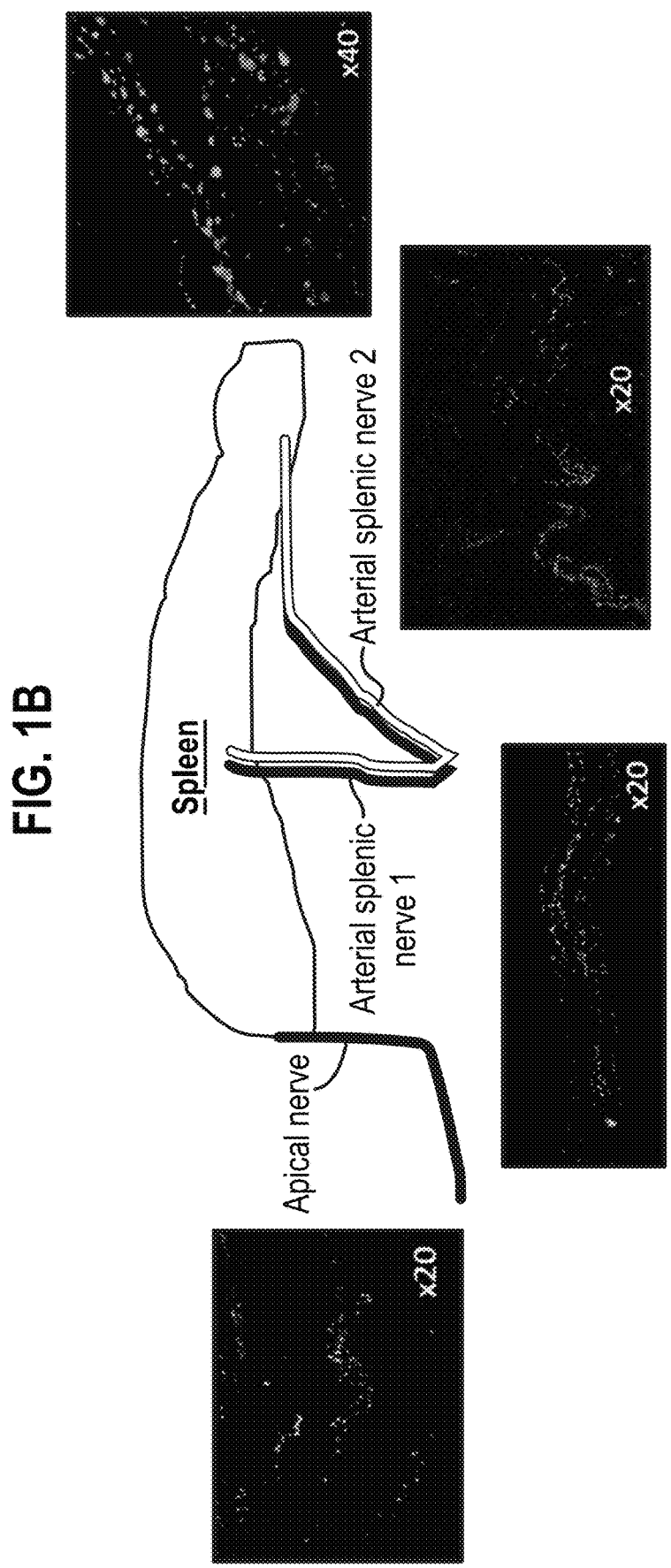
FIG. 1B shows representative confocal microscopy images of different branches of the spleen innervation in transgenic TH-Ires-Cre C57/B16 mice. Positive staining: tdTomato+, representing catecholaminergic fibers.

The different branches of the spleen innervation and artery were imaged, and representative images from TH-Ires-Cre x Ai14 mice (n=3) are shown in FIG. 1B.

It was noted that, as expected, cellular bodies and axons from the celiac ganglion were tdTomato+(data not shown).

FIG. 1B shows that the arteriolar splenic nerves were tdTomato+, as expected. Interestingly, the apical splenic nerve also showed tdTomato expression suggesting that it was also catecholaminergic.

One of the limitations of the Cre/LoxP system is that the reporter gene may still be expressed in adults due to genetic recombination whereas the activity of the promoter may be lost in the early phase of the development. The functional ability of apical splenic nerve to release norepinephrine (NE) was therefore investigated.

C57/B16 (N=2, n=3-7 mice/group) mice were anesthetized and a hook electrode is placed onto the apical splenic nerve. Electrostimulation (650 µA, 2 ms pulse width, 2-minutes duration, 10 Hz) was applied to mice. The control mice were not electrostimulated. Spleen biopsies were collected immediately after electrical stimulation and snap frozen in liquid nitrogen for NE ELISA measurements. A Mann-Whitney test was applied.

Figure 2:
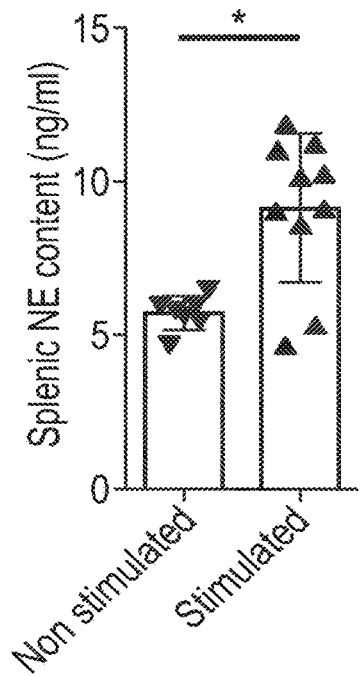
FIG. 2 shows the splenic norepinephrine (NE) levels compared between mice that had and had not been electrostimulated at the apical splenic nerve. A Mann-Whitney test was applied (*=statistically significant).

The results are shown in FIG. 2. It can be seen that a two-fold increase of the NE splenic content following stimulation was observed, confirming the catecholaminergic nature of these fibers.

Electrical Stimulation of the Splenic Nerves on LPS-Induced Inflammation in Anesthetized Mice The functional role of the splenic apical nerve on LPS-induced inflammation in anesthetized mice was investigated.

Figure 3A:
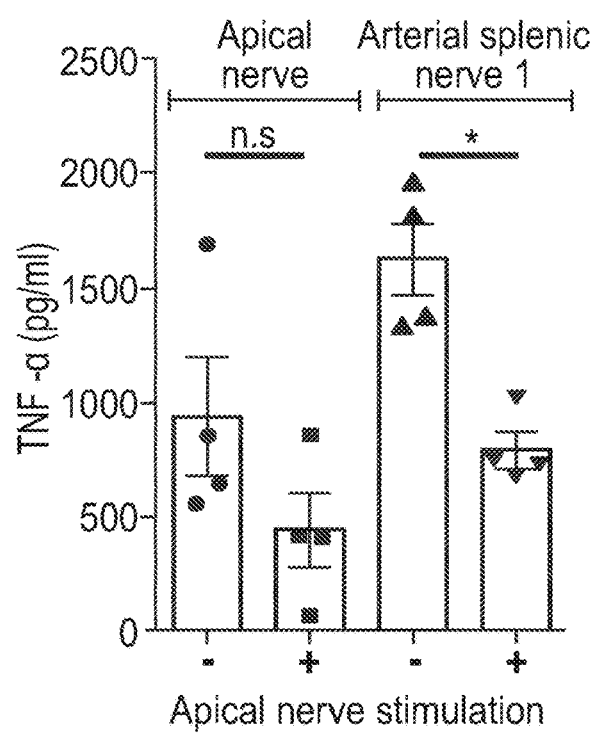
FIG. 3 shows the LPS-induced TNF and IL-6 levels in serum compared between mice that had and had not been electrostimulated at the apical splenic nerve or at the arterial splenic nerve. One representative experiment is shown in FIG. 3A (n=4), and a pool of 7 independent experiments are shown in FIGS. 3B (TNF) and 3C (IL-6) (each experiment: 4-7 animals/group). A one-way (A) or two-way (B and C) ANNOVA with Bonferroni multiple comparison test was applied (*=statistically significant).
Figure 3B:
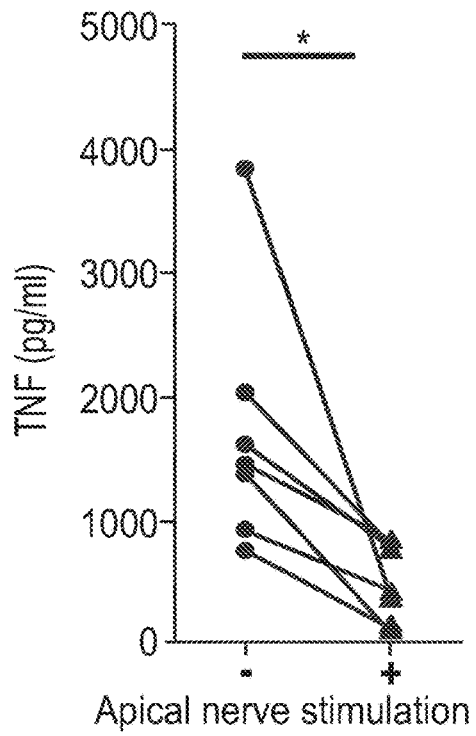
Figure 3C:
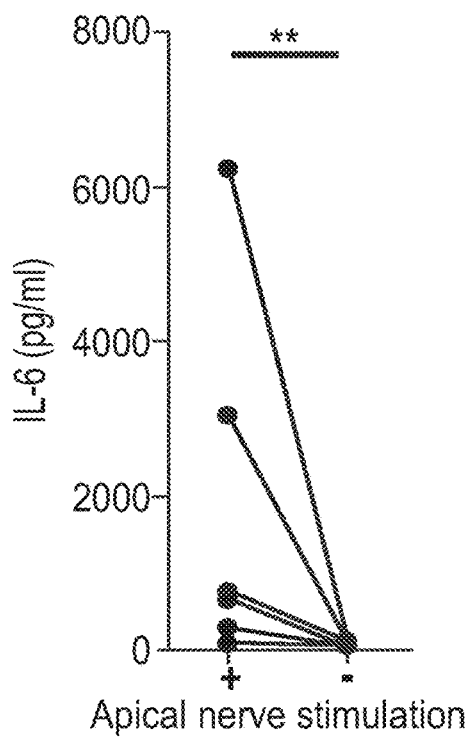

C57/B16 mice were anesthetized and a hook electrode is placed onto either the apical splenic nerve or the arterial splenic nerves. These mice were injected ip with 100 µg of LPS and electrostimulation (650 µA, 2 ms pulse width, 2-minutes duration, 10 Hz) were applied at the same time. Control mice did not receive electrostimulation. Sera were collected 90 minutes after LPS injection and assessed for TNF and IL-6. The results are shown in FIG. 3. FIG. 3A shows one representative experiment (n=4), and FIGS. 3B and 3C show a pool of 7 independent experiments, respectively, and in each experiment 4-7 animals/group. A one-way (A) or two-way (B and C) ANNOVA with Bonferroni multiple comparison test was applied.

FIG. 3 shows that, as expected, electrostimulation of the arterial splenic nerves in anesthetized animals resulted in markedly reduced serum levels of TNF and IL-6 after LPS injection. Interestingly, apical nerve electrostimulation also significantly reduced LPS-induced TNF and IL-6 secretions.

Resection of the Apical Nerve to the Spleen Results in Increased Inflammatory Cytokines Secretion in Anesthetized Mice In order to confirm that electrostimulation of the apical splenic nerve was contributing to the effect, and that it is not mediated by current leakage to other nerves or organs (e.g. spleen), the apical splenic nerve was resected.

C57/B16 mice were anesthetized and apical nerve of the spleen was cut or sham operated. These animals were injected ip with 100 µg of LPS. Sera was collected 90 minutes after LPS injection and assessed for TNF and IL-6 cytokine levels by ELISA.

Figure 4C:
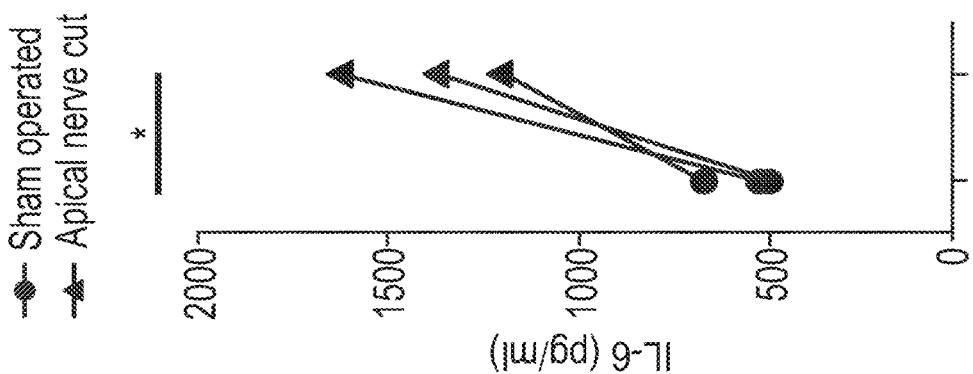
FIG. 4 shows the LPS-induced TNF and IL-6 levels in serum compared between apical splenic nerve resected mice and apical splenic nerve intact mice. A representative experiment is shown in FIG. 4A for each cytokine (n=4-5), and a pool of 5 (TNF) and 3 (IL-6) independent experiments are shown in FIGS. 4B and 4C, respectively (each experiment: 3-5 animals/group). A one-way (A) or two-way (B and C) ANNOVA with Bonferroni multiple comparison test was applied (*=statistically significant).
Figure 4B:
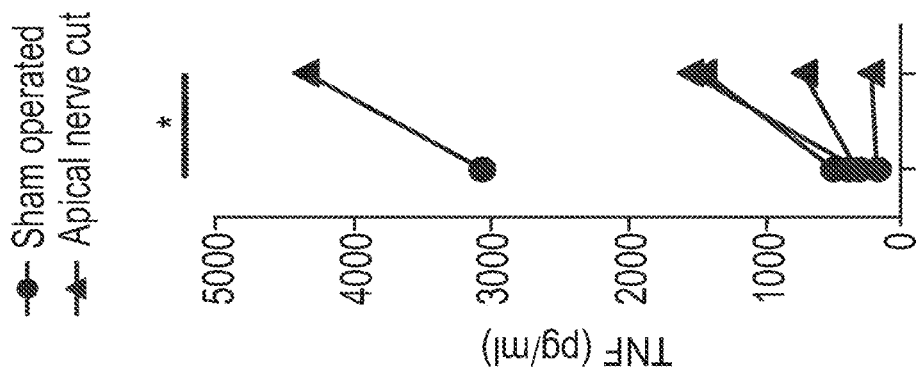
Figure 4A:
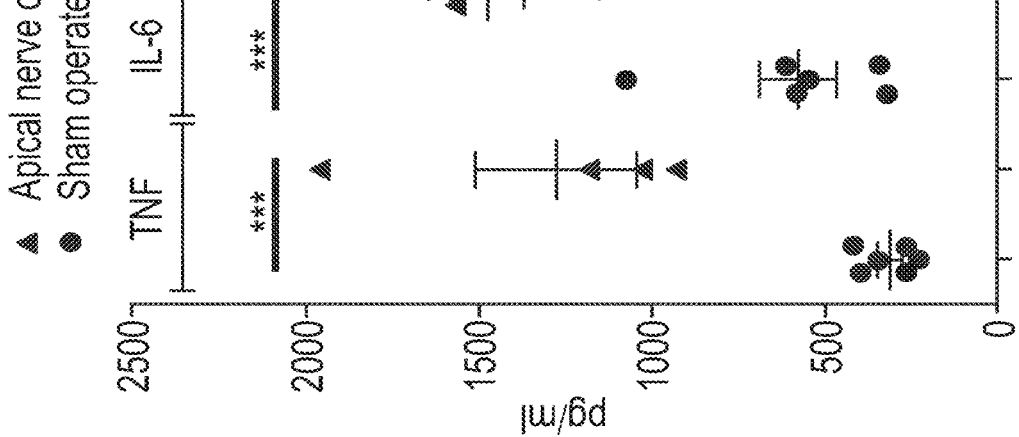

The results are shown in FIG. 4. FIG. 4A shows a representative experiment for each cytokine (n=4-5). FIGS. 4B and 4C show a pool of 5 (TNF) and 3 (IL-6) independent experiments, respectively, with in each experiment 3-5 animals/group. A one-way (A) or two-way (B and C) ANNOVA with Bonferroni multiple comparison test was applied.

FIG. 4 shows that ablation of the apical splenic nerve resulted in increased levels of LPS-induced inflammatory cytokine release in anesthetized animals. Therefore, the apical splenic nerve contributed to the physiological anti-inflammatory reflex.

Impact of Electrical Stimulation of the Apical Splenic Nerve on Arterial Blood Pressure Stimulation of the vagus nerve was known to cause a drop in blood pressure. It was therefore investigated whether apical splenic nerve stimulation might have an impact on systemic arterial blood pressure.

C57/B16 mice were anesthetized and a hook electrode was placed onto the apical splenic nerve. Cardiovascular parameters (heart rate (HR), blood pressure (BP)) were recorded before (pre-stim.) and after (post-stim.) electrical stimulation (2 ms pulse width, 2-minutes duration). Frequencies tested: 5, 10, and 20 Hz. Amplitudes tested: 0.3, 0.6, 1, and 5 mA. Stimulation of the vagus nerve (VNS, 10 Hz, 600 µA, 2 ms, 2 min) was used as control.

Figure 5A:
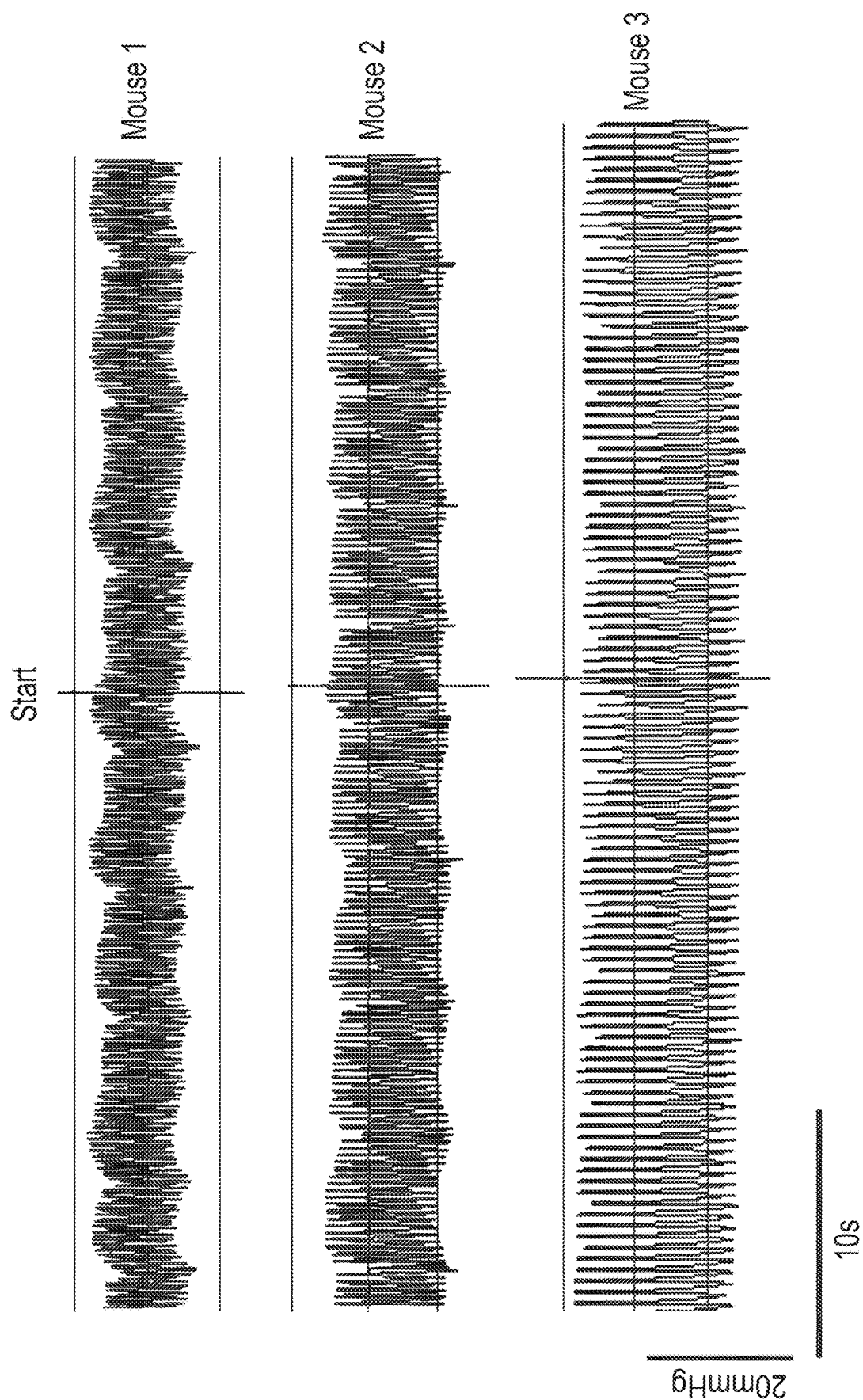
FIG. 5A shows a representative recording of the arterial blood pressure in three anesthetized mice. "Start" denotes the beginning of electrostimulation.

One representative recording is presented in FIG. 5A, and the HR, mean BP, maximum BP and minimum BP is pooled from three independent mice, as shown in FIG. 5B.

It was found that electrostimulation of the apical splenic nerve had minimal impact on arterial blood pressure or heart rate, irrespective of the electrical parameters applied. In contrast, electrostimulation of the vagus nerve significantly decreased the arterial blood pressure and heart rate.

Impact of Electrical Stimulation of the Apical Splenic Nerve on Cytokines and Chemokine Secretion The impact of electrical stimulation of the apical nerve on other cytokines and chemokine secretion in the blood was also investigated.

C57/B16 mice (4 mice/group) were anesthetized and a hook electrode is placed onto the apical splenic nerve. The animals were injected iv with 100 µg of LPS and electrostimulation (350 µA, 2 ms pulse width, 2-minutes duration, 1 Hz or 10 Hz) was applied at the same time. The control mice did not receive electrostimulation. Sera was collected at 60, 90 and 120 minutes after LPS injection and assessed for cytokine and chemokine levels. Pro-inflammatory cytokines (TNF, IL-12, IL-1β, CXCL1 and IL-6) and anti-inflammatory cytokine (IL-10) levels were assessed. FIG. 6 shows one representative experiment out of 2 (n=5-6 animals/group).

It was found that inflammatory cytokines (TNF, IL-12, IL-1β, CXCL1 and IL-6) secreted in the blood were dramatically reduced by electrical stimulation of the apical splenic nerve. In contrast, the anti-inflammatory cytokine IL-10 was increased at 120 min post electrical stimulation of the apical splenic nerve using 10 Hz.

Optimization of Electrical Stimulation Parameters in Anesthetized Mice

To evaluate the therapeutic potential of apical nerve electrical stimulation in conscious animals, the electrical stimulation was optimized in these animals.

Figure 7:
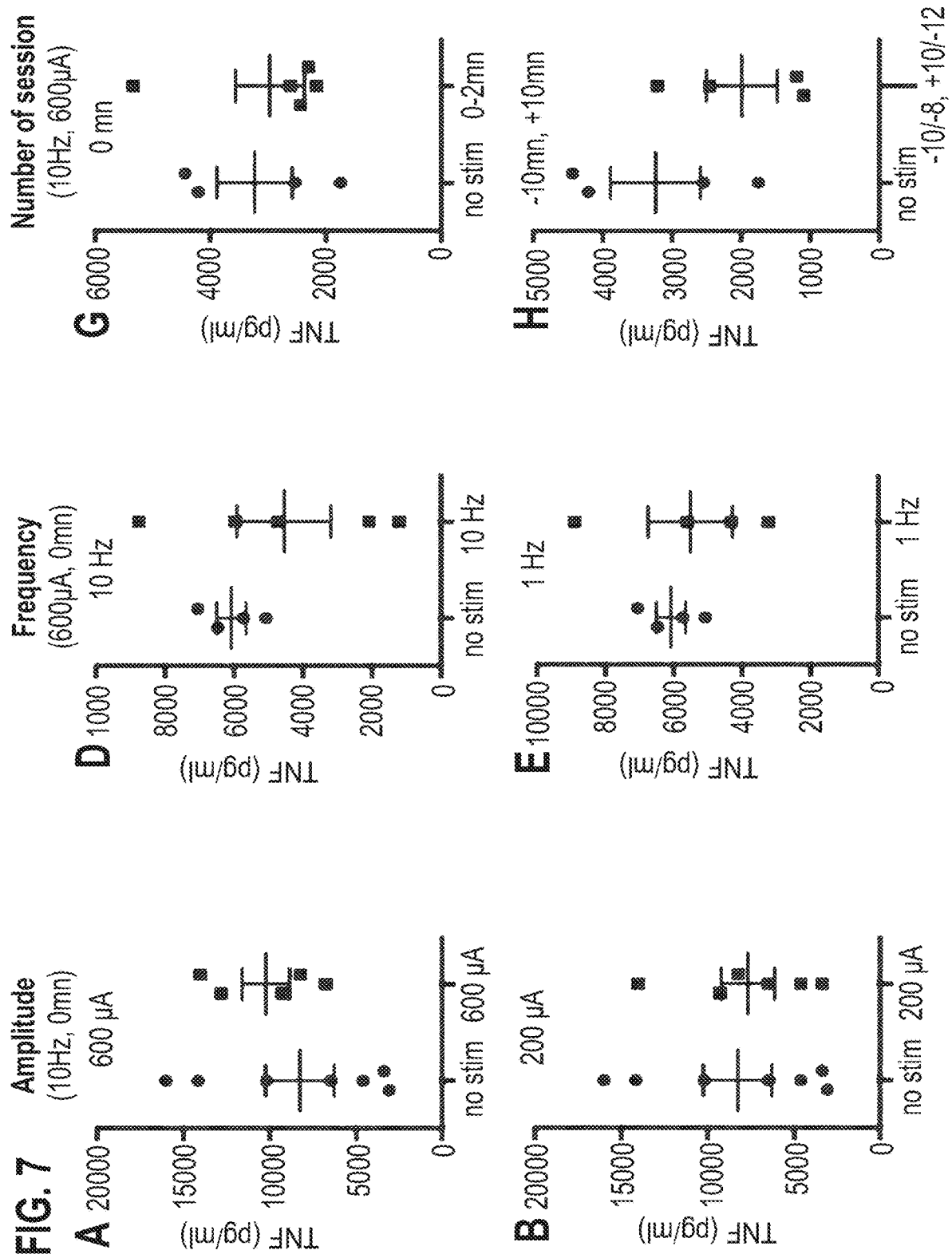
FIG. 7 shows the LPS-induced TNF levels in serum compared between mice that had and had not been electrostimulated at the apical splenic nerve at various conditions. One representative experiment is shown with at least 3 mice/group per condition. Amplitude tested at 10 Hz, t=0: 200 μA (B), 600 μA (A), and 1 mA (C). Frequency tested at 600 μA, t=0: 1 Hz (E), 10 Hz (D) and 20 Hz (F). Number of sessions tested at 10 Hz and 600 μA: one session at t=0 (G), two sessions at t=−10 min and t=+10 min (H), and three sessions at t=−10 min, t=0 min and t=+20 min (I). Starting times of electrostimulation are indicated in minutes relative to LPS injection.

C57/B16 mice were anesthetized and a Cortec electrode was implanted onto the apical splenic nerve. Five days following surgery, these animals were injected ip with 100 µg of LPS and electrostimulation (2 ms pulse width) was applied with various amplitude, frequency and number of session. Amplitude tested: 200 µA, 600 µA, and 1 mA. Frequency tested: 1 Hz, 10 Hz and 20 Hz. Number of sessions tested: one session at t=0, two sessions at t=−10 min and t=+10 min, and three sessions at t=−10 min, t=0 min and t=+20 min. Starting times of electrostimulation are indicated in minutes relative to LPS injection. Sera was collected at 90 minutes after LPS injection and assessed for TNF levels. Implanted but non-stimulated animals were used as control. One representative experiment is shown in FIG. 7 with at least 3 mice/group per condition.

Interestingly, three sessions of stimulation of 2 minutes applied −10 minutes, 0, and +20 minutes after LPS injection resulted in over 50% reduction of TNF secretion after LPS challenge (FIG. 7J). This inhibition was confirmed in seven independent experiments and was compared to the stimulation of periarteriolar-associated nerves.

Electrical Stimulation of Apical and Arterial Splenic Nerves Inhibits LPS-Induced Inflammation in Conscious Animals.

C57/B16 mice were anesthetized and Cortec electrodes were implanted either onto the apical or onto the periarteriolar splenic nerves (1 and 2). Five days following surgery, these animals were injected ip with 100 µg of LPS and electrostimulation (650 µA, 10 Hz, 2 ms pulse width, 2 min) was applied starting at −10, 0 and +20 minutes relative to LPS injection. Sera was collected at 90 minutes after LPS injection and assessed for TNF levels. Controls consist of fully Cortec implanted mice, which did not receive electrical stimulation.

The results are shown in FIG. 8. FIG. 8A shows the TNF levels (pg/ml) per group/mouse. Number of experiments (N) and total number of mice (n) are indicated, each group consisted of n=4-7 mice. FIG. 8B shows the same data expressed as percent of inhibition of TNF compared to control mice. It was found that all nerves tested were efficient in inhibiting LPS-induced TNF secretion, with the arterial splenic nerve 1 providing the best inhibition, followed by apical splenic nerve. The apical splenic nerve provided ~45% inhibition of LPS-induced TNF secretion.

Electrical Stimulation of Apical Splenic Nerve Improves Survival Following Endotoxemic Shock It was investigated whether mice having its apical splenic nerve implanted with Cortec electrodes would survive after injection of a lethal dose of LPS by intraperitoneal route.

C57/B16 mice were anesthetized and Cortec electrodes were implanted onto the apical splenic nerve. Five days following surgery, the animals were injected i.p. with a lethal dose of LPS (400 µg/animal) and electrostimulation (650 µA, 10 Hz, 2 ms pulse width) was applied for 2 minutes at −10, 0, +20 minutes relative to LPS challenge. Sera were collected at 90 min after LPS injection and assessed for TNF levels. The animals were then electrically stimulated with the same parameters at 16, 20, 24, 30, 34 and 38 hours after LPS injection. Survival was followed over 4 days. Controls consist of Cortec implanted mice, which did not receive electrical stimulation. One experiment is presented in FIG. 9 with at least 4 mice/group.

Figure 9A:
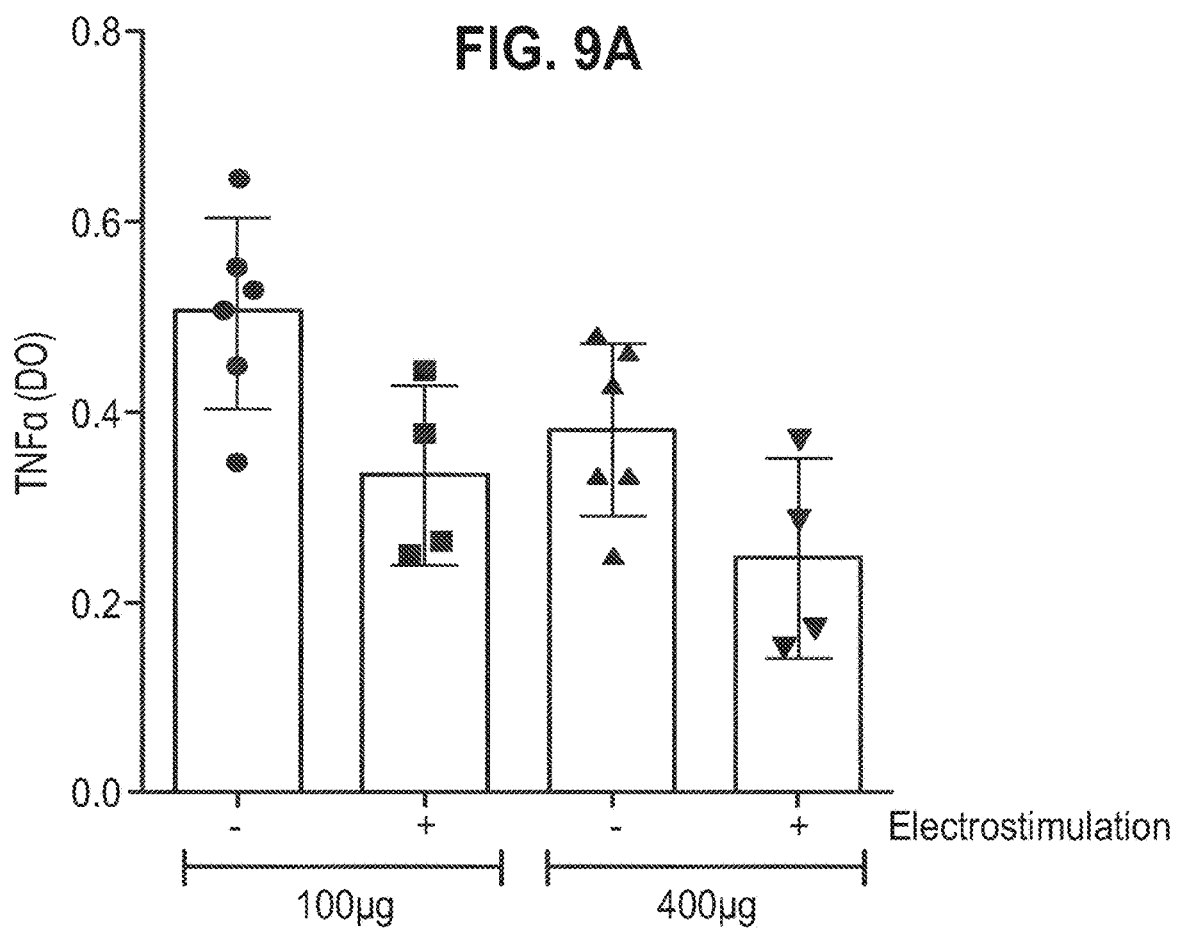
FIG. 9A shows the LPS-induced TNF levels in serum compared between conscious mice that had and had not been electrostimulated at the apical splenic nerve. Mice were injected ip with a lethal dose of LPS (400 μg/animal) or a sublethal dose of LPS (100 μg/animal).

FIG. 9A shows that LPS-induced TNF secretion was decreased when the mice were electrically stimulated at its apical splenic nerve. Although to a lesser extent, electrical stimulation of the apical splenic nerve still led to decreased TNF secretion following LPS lethal dose (400 µg/mouse) administration compared to LPS sublethal dose (100 µg/mouse).

Figure 9B:
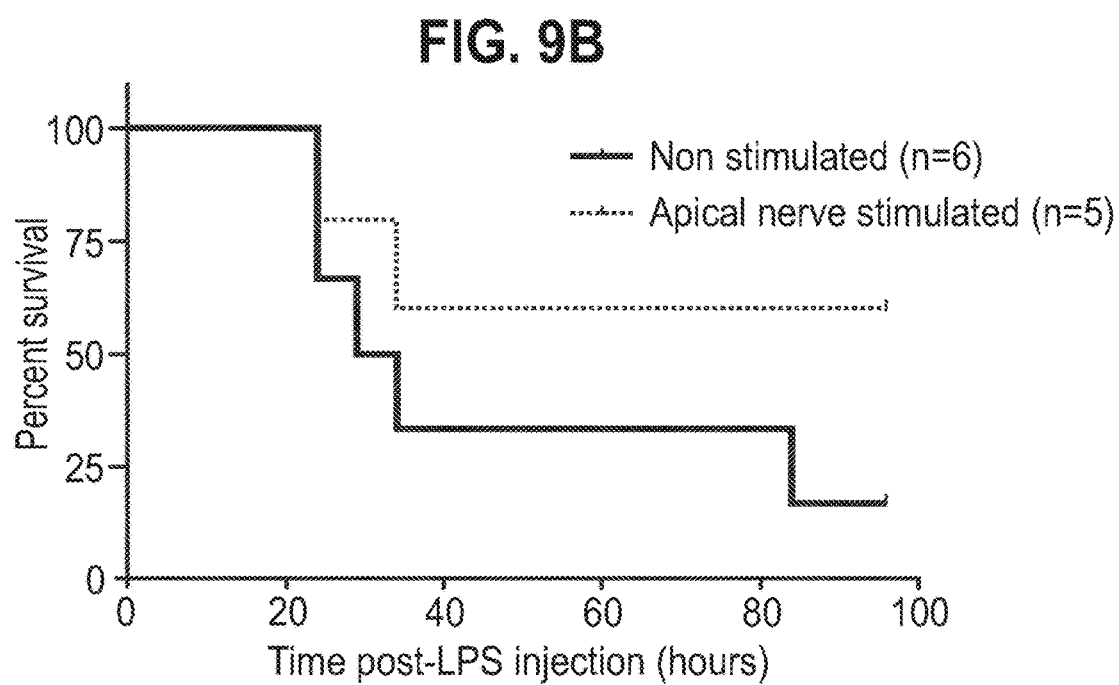
FIG. 9B shows the percentage survival of apical nerve stimulated mice compared to non-stimulated mice over time. One experiment is presented with at least 4 mice/group.
Figure 10:
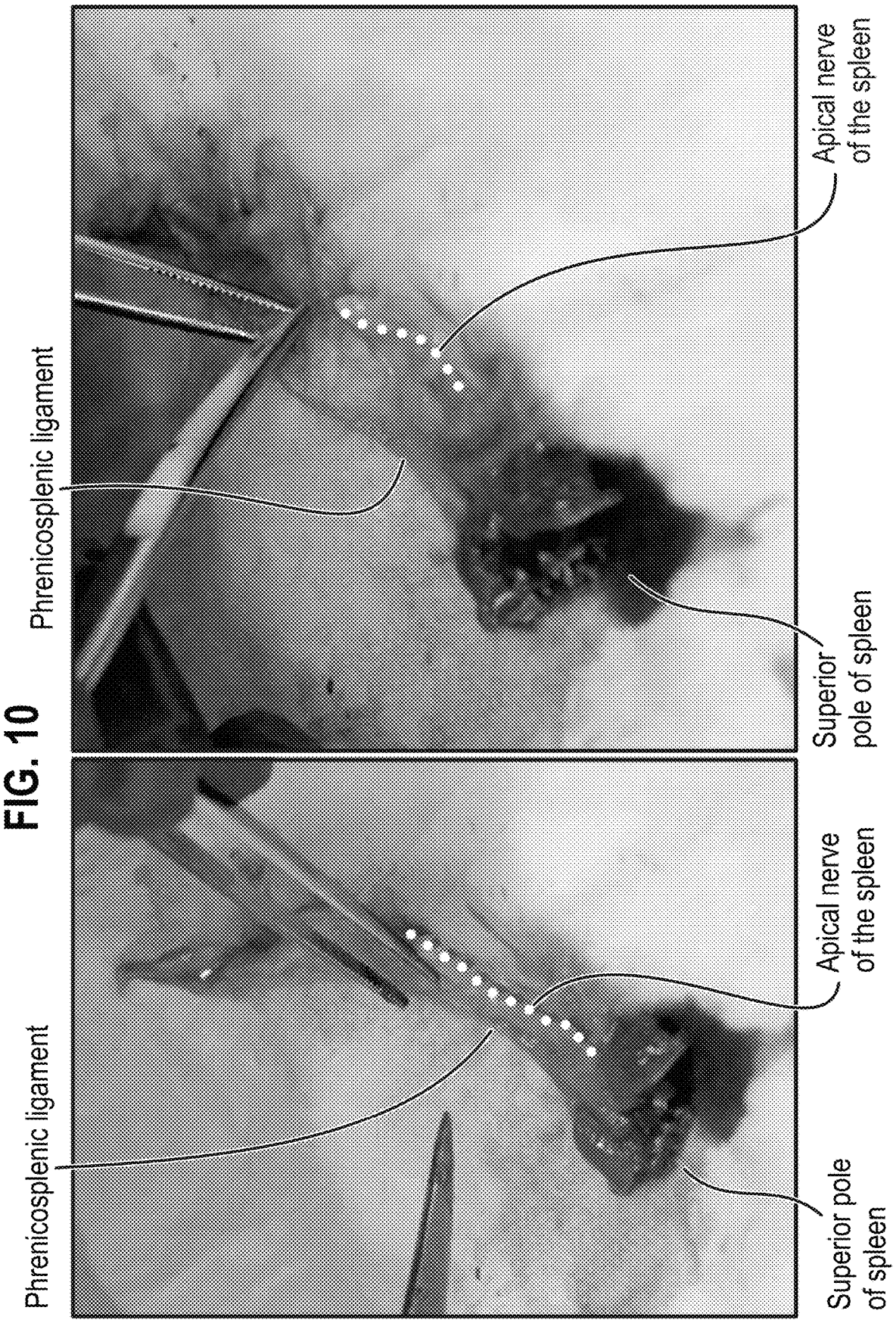
FIG. 10 is an image showing the location of the apical splenic nerve in humans relative to the superior pole of the spleen and the phrenicosplenic ligament.

FIG. 9B shows that three out of five mice (60%) survived in the electrostimulated group compared to one out of six (16.7%) in the control group following LPS administration.

CONCLUSION

In summary, the inventors found that an apical splenic nerve in mice was catecholaminergic. When electrically stimulated, this nerve was effective in inhibiting LPS-induced cytokine release in both anesthetized and conscious animals, and this effect was as potent as the periarteriolar branches of the splenic nerve. Interestingly, electrostimulation of the apical splenic nerve had minimal impact on the arterial pressure or heart rate. Electrical stimulation of the apical splenic nerve was also able to improve the survival following endotoxemic shock. Therefore, the inventors found that electrical stimulation of the splenic nerves, in particular, an apical splenic nerve, would be effective in treating inflammatory conditions, including autoimmune disorders (e.g. rheumatoid arthritis) and sepsis.

REFERENCES

[1] R. Medzhitov, Nature 454, 428-435 (24 Jul. 2008)
[2] J. M. Huston et al., J Exp Med 203, 1623.
[3] D. M. Nance, V. M. Sanders, Brain Behav Immun 21, 736.
[4] H. H. Dale, H. W. Dudley, J Physiol 68, 97.
[5] C. Cailotto et al., Neurogastroenterol Motil 24, 191.
[6] M. Rosas-Ballina, K. J. Tracey, Neuron 64, 28.
[7] G. Vida, G. Pena, E. A. Deitch, L. Ulloa J Immunol 186, 4340.
[8] B. O. Bratton et al., Exp Physiol 97, 1180.
[9] D. Martelli, S. T. Yao, M. J. McKinley, R. M. McAllen, J Physiol 592(7), 1677.
[10] D. Martelli, S. T. Yao, J. Mancera, M. J. McKinley, R. M. McAllen, Am J Physiol Regul Integr Comp Physiol 307, R1085.
[11] D. Martelli, M. J. McKinley, R. M. McAllen, Auton Neurosci. 182, 65.
[12] Koopman F A et al., Proc Natl Acad Sci USA, 19; 113(29):8284.
[13] US 2006/0287678.
[14] US2005/0075702.
[15] US20050075701.
[16] Buijs R M, et al., PLoS One. 2008 Sep. 5; 3(9):e3152.
[17] US 2015/0174397.
[18] US 2011/0160798.

The invention claimed is:

1. A device or system for stimulating neural activity of an apical splenic nerve, the device or system comprising:
at least one transducer configured for placement on or around the apical splenic nerve, wherein the apical splenic nerve is a non-arteriolar associated nerve located at an apex of a spleen, wherein the apical splenic nerve enters a superior pole of the spleen,
memory for storing patient specific physiological data pertaining to levels of signaling molecules secreted from the spleen, and
a signal generator configured for generating at least one signal to be applied to the apical splenic nerve via the at least one transducer wherein the at least one signal stimulates or inhibits the neural activity of the apical splenic nerve to produce a physiological response in a subject, wherein the physiological response is one or more of the group consisting of: a reduction in pro-inflammatory cytokines, an increase in anti-inflammatory cytokines, an increase in catecholamines, changes in immune cell population or immune cell surface co-stimulatory molecules, a reduction in factors involved in an inflammation cascade or a reduction in immune response mediators; and wherein the at least one transducer is at least one electrode, and the signal generator is a voltage or current source configured to generate an electrical signal to be applied to the apical splenic nerve via the at least one electrode, and wherein the electrical signal has a frequency of between 1 and 50 Hz.

2. The device or system of claim 1, wherein the at least one transducer is configured to attach onto the apical splenic nerve.

3. The device or system of claim 1, wherein the electrical signal is an AC signal.

4. The device or system of claim 1, wherein the electrical signal comprises one or more pulse trains, each comprising a plurality of square or sawtooth pulses, wherein the plurality of pulses are delivered at a frequency in a range of 1 to 50 Hz.

5. The device or system of claim 4, wherein the plurality of pulses are delivered at a frequency of 1 Hz, 5 Hz or 10 Hz.

6. The device or system of claim 4, wherein the square or sawtooth pulses have a duration of between 10 μs and 5 ms.

7. The device or system of claim 4, wherein the square or sawtooth pulses are bipolar pulses.

8. The device or system of claim 4, wherein the square or sawtooth pulses have a constant current of between 200 μA and 5 mA.

9. The device or system of claim 8, wherein the square or sawtooth pulses have a constant current of 600 μA.

10. The device or system of claim 4, wherein the at least one signal is delivered for between 30 seconds and 5 minutes.

11. The device or system of claim 10, wherein the signal is delivered for 2 minutes.

12. The device or system of claim 4, wherein the square or sawtooth pulses have a duration of between 20 μs and 4 ms.

13. The device or system of claim 4, wherein the square or sawtooth pulses have a duration of between 50 μs and 2 ms.

14. The device or system of claim 4, wherein the square or sawtooth pulses have a duration of between 100 μs and 1 ms.

15. The device or system of claim 4, wherein the square or sawtooth pulses have a duration of between 200 μs and 500 μs.

16. The device or system of claim 4, wherein the electrical signal comprises one or more pulse trains, each comprising a plurality of square or sawtooth pulses, wherein the plurality of pulses are delivered at a frequency between 1 and 30 Hz.

17. The device or system of claim 1, further comprising a detection subsystem for detecting one or more sensory signals indicative of excessive or insufficient levels of a cytokine and, upon detection of the one or more sensory signals, cause the at least one signal to be applied to an apical splenic nerve via the at least one electrode.

18. The device or system of claim 17, further comprising a memory for storing data pertaining to sensory signals indicative of normal, excessive or insufficient levels of a cytokine, the detection subsystem configured to compare the one or more detected sensory signals with the data.

19. The device or system of claim 1, further comprising a signaling subsystem for receiving a control signal from a controller and, upon detection of the one or more control signals, cause the electrical signal to be applied to the apical splenic nerve via the at least one electrode.

20. The device or system of claim 1, wherein the signal generator is configured to apply the electric signal periodically.

21. The device or system of claim 1, wherein the device is configured to be attached to the apical splenic nerve and wherein the device is positioned such that the at least one transducer is in signaling contact with the apical splenic nerve, so the apical splenic nerve can be distinguished from the apical splenic nerve in its natural state, and wherein the apical splenic nerve is located in a patient who suffers from an inflammatory disorder.

22. The device or system of claim 1, wherein the device is configured to be attached to the apical splenic nerve and wherein the device is positioned such that a nerve membrane is reversibly depolarised or hyperpolarised by an electric field, such that an action potential is generated de novo in a modified nerve.

23. The device or system of claim 1, wherein the device is configured to be attached to the apical splenic nerve and wherein the device is positioned such that an action potential is propagated along the apical splenic nerve in a normal state; wherein at least a portion of the apical splenic nerve is subject to an application of a temporary external electrical field which modifies a concentration of potassium and sodium ions within the apical splenic nerve, causing depolarization or hyperpolarization of a nerve membrane, thereby, in a disrupted state, temporarily generating an action potential de novo across that portion; wherein the apical splenic nerve returns to its normal state once the temporary external electrical field is removed.

24. The device or system of claim 1, wherein the device is configured to be attached to the apical splenic nerve and wherein the device is positioned such that a portion of the apical splenic nerve is subject to application of a temporary external electrical field forms.

25. The device or system of claim 1, wherein the device modulates neural activity of the apical splenic nerve.

26. A method of reducing inflammation in a subject by reversibly stimulating neural activity of an apical splenic nerve, comprising: (i) implanting a device configured for stimulating neural activity of an apical splenic nerve into a patient, the device including memory for storing patient specific physiological data pertaining to levels of signaling molecules secreted from a spleen, wherein the apical splenic nerve is a non-arteriolar associated nerve located at an apex of the spleen, wherein the apical splenic nerve enters a superior pole of the spleen; (ii) positioning a transducer in signaling contact with an apical splenic nerve; and (iii) activating the device.

27. The method of claim 26, wherein said subject suffers from an inflammatory disorder.

28. A method of reversibly stimulating neural activity in an apical splenic nerve, comprising: (i) implanting a device configured for stimulating the neural activity of an apical splenic nerve into a patient, the device including memory for storing patient specific physiological data pertaining to levels of signaling molecules secreted from a spleen; (ii) positioning a transducer in signaling contact with an apical splenic nerve, wherein the apical splenic nerve is a non-arteriolar associated nerve located at an apex of the spleen, wherein the apical splenic nerve enters a superior pole of the spleen; and (iii) activating the device.

29. A method of treating in a subject who suffers from, or is at risk of, inflammatory disorder, comprising (i) implanting a device configured for stimulating neural activity of an apical splenic nerve into a patient, the device including memory for storing patient specific physiological data pertaining to levels of signaling molecules secreted from a spleen; (ii) positioning a transducer in signaling contact with an apical splenic nerve, wherein the apical splenic nerve is a non-arteriolar associated nerve located at an apex of the spleen, wherein the apical splenic nerve enters a superior pole of the spleen; and (iii) activating the device.

30. A method of controlling a device configured for stimulating the neural activity of an apical splenic nerve, the device including memory for storing physiological data pertaining to normal levels of signaling molecules secreted from the spleen, wherein the device is in signaling contact with an apical splenic nerve, comprising steps of:
  storing in memory patient specific physiological data pertaining to levels of signaling molecules secreted from the spleen;
  sending control instructions to the device;
  applying a signal to the apical splenic nerve, wherein the apical splenic nerve is a non-arteriolar associated nerve located at an apex of the spleen, wherein the apical splenic nerve enters a superior pole of the spleen;
  detecting a signal received from one or more sensors; and
  comparing the signal received from the one or more sensors with the physiological data stored in the memory to determine whether the signals are indicative of insufficient or excessive levels of a signaling molecule secreted from the spleen.

* * * * *